(12) United States Patent
Schmitt-Milas et al.

(10) Patent No.: US 7,999,096 B2
(45) Date of Patent: Aug. 16, 2011

(54) ANTI-MYOSIN VA SIRNA AND SKIN DEPIGMENTATION

(75) Inventors: Anne-Marie Schmitt-Milas, Tournefeuille (FR); Jo Lambert, De Pinte (BE); Wendy Westbroek, Rockville, MD (US); Mireille Van Gele, Adegem (BE)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 78 days.

(21) Appl. No.: 12/086,242

(22) PCT Filed: Dec. 12, 2006

(86) PCT No.: PCT/EP2006/069618
§ 371 (c)(1),
(2), (4) Date: Jun. 9, 2008

(87) PCT Pub. No.: WO2007/068704
PCT Pub. Date: Jun. 21, 2007

(65) Prior Publication Data
US 2009/0239934 A1    Sep. 24, 2009

(30) Foreign Application Priority Data
Dec. 12, 2005  (FR) ....................... 05 12553

(51) Int. Cl.
*C07H 21/04* (2006.01)
(52) U.S. Cl. ................... 536/24.5; 536/24.31; 536/24.1; 514/44
(58) Field of Classification Search .......... None
See application file for complete search history.

(56) References Cited

U.S. PATENT DOCUMENTS
2005/0137151 A1* 6/2005 Binetti et al. ............. 514/44
2008/0113351 A1* 5/2008 Naito et al. ............... 435/6

FOREIGN PATENT DOCUMENTS
WO  WO-2005/060536 A1  7/2005

OTHER PUBLICATIONS

Briganti et al. Chemical and Instrumental Approaches to Treate Hyperpigmentation. Pigment Cell Res 16: 101-110, 2003.*
Westbroek et al. Interactions of human myosin Va isoforms, endogenously expressed in human melanocytes, are tightly regulated by the tail domain. J. Invest Dematol. 120: 465-475, 2003.*
Edgar et al., "Inhibition of dendrite formation in mouse melanocytes transiently transfected with antisense DNA to myosin Va," Journal of Anatomy, vol. 195, 1999, pp. 173-184.
Mittal, "Improving the efficiency of RNA interference in mammals," Nature Reviews, vol. 5, 2004, pp. 355-365.
Dorsett et al., "Sirnas: Applications in Functional Genomics and Potential AS Therapeutics," Nature, vol. 3, No. 4, 2004, pp. 318-329.
Reynolds et al., "Rational siRNA design for RNA interference," Nature Biotechnology, vol. 22, No. 3, 2004, pp. 326-330.
Leung et al., "RNA interference: From gene silencing to gene-specific therapeutics," Pharmacology and Therapeutics, vol. 107, No. 2, 2005, pp. 222-239.
Peter et al., "Mammalian RNAI: A Practical Guide," Biotechniques, vol. 39, No. 2, 2005, pp. 215-224.

* cited by examiner

*Primary Examiner* — Kimberly Chong
(74) *Attorney, Agent, or Firm* — Birch, Stewart, Kolasch and Birch, LLP

(57) ABSTRACT

The present invention relates to novel isolated siRNAs comprising a sense RNA strand and a complementary antisense RNA strand which together form an RNA duplex, characterized in that the sense RNA strand comprises a sequence which has at most one nucleotide that is distinct in relation to a fragment of 14 to 30 contiguous nucleotides of the nucleotide sequence of exon F of the gene encoding the myosin Va protein, and also to compositions comprising at least one such siRNA, and to the use of at least one such siRNA as a cosmetic or therapeutic agent for skin depigmentation.

14 Claims, 11 Drawing Sheets

A

```
  1 cgtcaagaac tagaatcaga aaacaaaaca ctgaagaatg agccaaatga gttgcgcaag
 61 gccctcagtg agaaaagtgc cccagaggtg accgcccag gtgcacctgc ctaccgtgtc
121 ctcatggagc agctgacctc tgtgagcgag gagcttgatg tccgcaagga ggaagtcctc
181 atcctaaggt ctcaactggt gagccagaaa gaggccatcc aacccaagga tgacaagaat
241 acaatgacag atcccacaat acttctggaa gatgtacaaa aaatgaaaga taaaggtgaa
301 atagcacaag catacattgg tttgaaagaa acaaatagat catctgctct ggattaccat
361 gagttgaatg aggatggaga gctgtggctg gtttatgaag ggttaaaaca agccaacagg
421 ctcctggaat cccagctgca gtcacagaag aggagccatc agaatgaggc cgaggccctc
481 cgtggggaga tccagagcct gaaggaggag aacaaccgac agcagcagct gctggcccag
541 aacctgcagc tgccccaga ggcccgcatt gaggccagcc tgcagcaoga gatcacccgg
601 ctgaccaacg aaaacttgta ctttgaggaa ttatatgcag atgaccctaa gaagtatcaa
661 tcatatcgga tttcccttta caaacggatg att
```
                                                                    exon F

B siRNA1                    siRNA3

5' tattttgaggaattatatgcagatgaccctaagaagtatcaatcatatcggatttccctttacaaacggatgatt 3' siRNA2

C siRNA1 =     UGACCCUAAGAAGUAUCAAdTdT
             dTdTACUGGGAUUCUUCAUAGUU siRNA2 =     GUAUCAAUCAUAUCGGAUUdTdT
             dTdTCAUAGUUAGUAUAGCCUAA siRNA3 =     UCAUAUCGGAUUUCCCUUUdTdT
             dTdTAGUAUAGCCUAAAGGGAAA

Figure 1

ANTI-MYOSIN VA SIRNA AND SKIN DEPIGMENTATION

This Application is the National Phase Under 35 U.S.C. §371 of PCT International Application No. PCT/EP2006/069618 which has an International filing date of Dec. 12, 2006, which claims priority to European Patent Office Application No. 0512553 filed on Dec. 12, 2005. The entire contents of all applications listed above are hereby incorporated by reference.

The present invention relates to new isolated siRNAs comprising a sense RNA strand and a complementary antisense RNA strand which together form an RNA duplex, characterised in that the sense RNA strand comprises a sequence which has at most one distinct nucleotide compared to a fragment of 14 to 30 contiguous nucleotides from the nucleotide sequence of exon F of the gene encoding myosin Va protein, and also relates to compositions comprising at least one such siRNA, and to the use of at least one such siRNA as a cosmetic or therapeutic agent for skin depigmentation.

Skin pigmentation is a complex process comprising many steps. Melanocytes, which are in the basal layer of epidermis, can be activated by internal or external stimuli (for example, exposure to ultraviolet (UV) radiation) to produce melanin in the specialised organelles related to lysosomes known as melanosomes. After maturation, perinuclear melanosomes are transported along microtubules and the actin cytoskeleton to the periphery of melanocytes dendrites. (Lambert J et al. Cell Mol Biol (Noisy-le-grand): 45: 905-18, 1999; Hara M et al. J Invest Dermatol.: 114:438-43, 2000; Vancoillie G et al. J Invest Dermatol.: 114: 421-9, 2000). Melanosomes, which comprise melanin, are then transferred to adjacent keratinocytes from the distal ends of dendrites by a mechanism that is as yet unknown.

Any change to a step in this complex process can lead to skin pigmentation disorders. In particular, an increase in the number of active melanocytes, and/or an increase in the production of melanin, and/or an increase in the transfer of melanosomes from melanocytes to keratinocytes can lead to hyperpigmentation (or dyschromatosis) of the skin. Such hyperpigmentation can be caused by many factors, such as drugs, sun, metabolic or nutritional dysfunctions, as well as by genetic or autoimmune diseases. This generally implies serious cosmetic and psychological consequences for the patient, who in many cases will seek out appropriate treatment.

Therefore, many efforts have been made to develop effective treatments for hyperpigmentation. Most existing chemical treatments comprise depigmenting agents that target melanin synthesis pathway, notably by inhibiting the activity of tyrosinase enzyme that is necessary for melanin synthesis. Such depigmenting agents notably include hydroquinone and its derivatives, retinol or tretinoin, ascorbic acid and its derivatives, placenta extracts, kojic acid, ferulic acid, arbutin, dihydroxybenzene derivatives (WO 00/47045), guaiacol derivatives (WO 00/47179), 4-(2,3-dihydroxyphenyl)-cyclohexanol (WO 00/56279), resorcinol derivatives (WO 00/56702), phenolic amides (WO 99/32077). These substances may present certain disadvantages. They can be unstable, need to be used at high concentrations, lack specificity in their mode of action, or be cytotoxic or irritant.

Physical types of treatments have also been developed, such as medium depth exfoliation, dermabrasion or laser therapy. However, these treatments are generally less effective and cause adverse secondary effects such as risk of post-inflammatory hypo- or hyperpigmentation, ochronosis, or scarring that can have carcinogenic results (Briganti S et al. Pigment Cell Res.: 16: 101-10, 2003; Halder R M, Nootheti P K. J Am Acad Dermatol.: 48: S143-48, 2003; Halder R M, Richards G M. Skin Therapy Lett.: 9:1-3, 2004).

So a need exists to develop novel cosmetic and/or therapeutic treatments of hyperpigmentation that are effective and reliable.

As well as chemical treatments, another possibility for obtaining the inhibition of gene expression consists in using antisense nucleic acids or making use of a process known as RNA interference (Dykxhoorn D M et al. Nat Rev Mol Cell Biol.: 4: 457-67, 2003; Soutschek J et al. Nature: 432: 173-8, 2004).

RNA interference (hereinafter referred to as RNAi) is the process by Which a double stranded RNA (dsRNA) with a given sense nucleic sequence leads to the breakdown of all messenger RNA (mRNA) comprising said nucleic sequence, in a manner specific to said nucleic sequence. Although the RNAi process was originally demonstrated in *Caenorhabditis elegans*, it is now clear that the RNAi process is a very general phenomenon, and inhibition of human genes by RNAi has been achieved.

The process of RNAi can be achieved using small interfering RNA (or siRNA). These siRNAs are dsRNA of fewer than 30 nucleotides comprising in their sense sequence a sequence that is highly homologous, preferably identical, to a fragment of the targeted mRNA. When a siRNA crosses the plasma membrane, the reaction of the cell is to destroy the siRNA and all the sequences comprising an identical or highly homologous sequence. Thus a mRNA with a fragment that is identical or highly homologous to the siRNA sequence will be destroyed, the expression of this gene being thus inhibited.

For the treatment of hyperpigmentation, it has been proposed in the prior art to use antisense oligonucleotides directed against the genes of tyrosinase or TRP-1 protein (WO 01/58918), or against the gene of the PKC β1 protein involved in the phosphorylation process of tyrosinase (WO 2005/073243). The use of siRNAs targeting the tyrosinase gene (WO 2005/060536) has also been proposed.

However, all these genes are involved in the melanin synthesis pathway, and no disclosure or suggestion has ever been made of siRNA targeting a gene involved, not in the melanin synthesis pathway, but in the transport of melanosomes within melanocytes and in their transfer to keratinocytes.

It has been shown, notably by the inventors, that myosin Va protein is involved in the transport of melanosomes within melanocytes. (Lambert J et al. Cell Mol Biol (Noisy-le-grand): 45: 905-18, 1999; Lambert et al. J Invest Dermatol.: 111: 835-40, 1998). More specifically, myosin Va protein has several splicing variants, and the variant comprising exon F is necessary for transporting melanosomes (Westbroek W et al. J Invest Dermatol.: 120: 465-75, 2003).

However, to date, no attempt has been made to inhibit the expression of the variant of myosin Va protein comprising exon F using siRNAs, or to apply this approach to the cosmetic or therapeutic treatment of hyperpigmentation.

The inventors found that it is possible to synthesise siRNAs targeting the exon F of the myosin Va protein and to induce, thanks to these siRNAs, an RNAi process specific to the exon F of the myosin Va protein. They also showed that said siRNAs are effective for inhibiting the expression of the variant of the myosin Va protein comprising exon F at concentrations of siRNAs that do not lead to a decrease in cell viability and that the effect is dose-dependant. Furthermore, the inventors also found that the presence of siRNAs targeting the exon F of the myosin Va protein enables the inhibition of the transfer of melanosomes from melanocytes to keratinocytes.

The present invention thus relates to a new isolated siRNA comprising a sense RNA strand and a complementary antisense RNA strand which together form a RNA duplex, characterised in that the sense RNA strand comprises a sequence which has at most one distinct nucleotide compared to a fragment of 14 to 30, advantageously 15 to 29, 16 to 28, 17 to 27, 18 to 25, 18 to 23, or 18 to 21 contiguous nucleotides of the nucleotide sequence of exon F of the gene encoding myosin Va protein. The expression "comprises a fragment of the nucleotide sequence of exon F of the gene encoding myosin Va protein" as used throughout the description of the invention is understood to mean an RNA sequence corresponding to the gene sequence, that is to say an RNA sequence that corresponds to the gene sequence in which the T are replaced by U.

The sense strand of a siRNA according to the invention thus comprises either a fragment of 14 to 30, advantageously 15 to 29, 16 to 28, 17 to 27, 18 to 25, 18 to 23, or 18 to 21 contiguous nucleotides of the nucleotide sequence of exon F of the gene encoding myosin Va protein, or a sequence with one distinct nucleotide compared to such a fragment. This is because the RNAi process is specific to the sequence, and a high sequence homology is needed for effective RNAi. Advantageously, the sense strand of RNA comprises a sequence identical to a fragment of 14 to 30, advantageously 15 to 29, 16 to 28, 17 to 27, or 18 to 25 contiguous nucleotides of the nucleotide sequence of exon F of the gene encoding the myosin Va protein.

Myosin Va protein has been described in different species, particularly humans, mice and rats. In an advantageous embodiment, the nucleotide sequence of exon F of the gene encoding myosin Va protein is the human sequence of exon F of myosin Va protein, which is represented by SEQ ID NO:1. The sequence of human myosin Va protein is represented in the FIG. 1A, with the portion corresponding to exon F (SEQ ID NO:1) underlined.

All siRNAs targeting a fragment of 14 to 30, advantageously 15 to 29, 16 to 28, 17 to 27, 18 to 25, 18 to 23, or 18 to 21 contiguous nucleotides with the sequence SEQ ID NO:1 are included in the scope of the invention. However, it is advantageous that the exon F fragment of the myosin Va protein that is being targeted, that is to say which has a sequence comprised in the sense strand of the siRNA, is not a fragment that has a characteristic structure in the mRNA of myosin Va protein or to which regulatory proteins can bind. The term "characteristic structure", as used in the present invention, is understood to mean a stem or loop or hairpin type structure that can form in an mRNA of the myosin Va protein. Several organisations offer different tools that are freely available on the Internet (see Table 1 below), and can be used to design siRNAs that target exon F of the human myosin Va protein.

TABLE 1

Internet sites with siRNA selection tools

| Organisation | Internet address |
|---|---|
| Ambion | http://www.ambion.com/techlib/misc/siRNA_design.html |
| Dharmacon | http://www.dharmacon.com/sidesign/ |
| Qiagen | http://www1.qiagen.com/Products/GeneSilencing/CustomSiRna/SiRnaDesigner.aspx |
| Emboss | http://bioweb.pasteur.fr/seqanal/interfaces/sirna.html |
| Tuschl Laboratory | http://www.rockefeller.edu/labheads/tuschl/sirna.html |
| The Whitehead | http://jura.wi.mit.edu/bioc/siRNAext/ |

Most companies marketing customised siRNAs guarantee the effectiveness of the siRNAs synthesised. Moreover, the effectiveness of all siRNA targeting exon F of the myosin Va protein can be verified by different tests, notably those described in detail in examples 1 and 2.

The inventors have synthesised and tested several specific siRNAs targeting different fragments of exon F of human myosin Va protein. In an advantageous embodiment of a siRNA according to the invention, the fragment of 14 to 30, advantageously 15 to 29, 16 to 28, 17 to 27, 18 to 25, 18 to 23, or 18 to 21 contiguous nucleotides of the nucleotide sequence of exon F of the gene encoding human myosin Va protein consists of a nucleotide sequence selected from SEQ ID NO:2, SEQ ID NO:3, and SEQ ID NO:4. The position of the three sequences SEQ ID NO:2, SEQ ID NO:3, and SEQ ID NO:4 is specified in FIG. 1B. In a particularly advantageous embodiment, the fragment of 14 to 30, advantageously 15 to 29, 16 to 28, 17 to 27, 18 to 25, 18 to 23, or 18 to 21 contiguous nucleotides of the nucleotide sequence of exon F of the gene encoding the myosin Va protein consists of the nucleotide sequence SEQ ID NO:3.

A siRNA according to the invention is a small double stranded RNA with sense and antisense strands paired by Watson-Crick bonds, and in which the sequence of the sense strand consists of or comprises a fragment of 14 to 30, advantageously 15 to 29, 16 to 28, 17 to 27, 18 to 25, 18 to 23, or 18 to 21 contiguous nucleotides of the nucleotide sequence of exon F of myosin Va protein.

It is known that siRNAs with a sequence composed of 30 to 50% of guanines and cytosines are more effective than sequences with a higher proportion of guanines and cytosines. Therefore the siRNAs according to the invention advantageously have a sequence composed of 30 to 50% of guanines and cytosines.

Is should be understood that a siRNA according to the invention can equally comprise two complementary single stranded RNA molecules, or a single single stranded RNA molecule in which two complementary portions are paired by Watson-Crick bonds and are linked covalently on one side by a hairpin type structure (this is more specifically known as shRNA for "short hairpin RNA"), which can be considered as a subclass of siRNA. Throughout the description, the term siRNA should be understood in its broad sense including shRNAs, unless otherwise indicated. In an advantageous embodiment, a siRNA according to the invention comprises two complementary single stranded RNA molecules. In another advantageous embodiment, a siRNA according to the invention comprises or consists of a single molecule of single stranded RNA in which two complementary portions are paired by Watson-Crick bonds and are linked covalently on one side by a hairpin type structure, that is to say it is a shRNA.

Moreover, the sense and/or antisense RNA strands can further comprise a 3' overhang fragment of 2 to 4 nucleotides, in particular when a siRNA according to the invention comprises two complementary single stranded RNA molecules. The expression "3' overhang fragment of 2 to 4 nucleotides" as used herein is understood to mean the presence in at least one strand of the RNA duplex of 2 to 4 nucleotides not paired with the complementary strand at the 3' distal end of said strand. The nucleotides used in the 3' overhang fragment can be natural nucleotides (ribonucleotides or deoxyribonucleotides), or modified nucleotides such as LNA (Locked Nucleic Acid) which comprises a methylene bridge between the 2' and 4' positions of the ribose (Soutschek J. et al. Nature. 2004 Nov. 11; 432(7014):173-8). The 3' overhang fragment can also undergo all types of chemical modification described in the following paragraph for the sense RNA strand and/or the antisense RNA strand of a siRNA according to the invention. Advantageously, the 3' overhang fragment consists of 2 nucleotides. In this case, the preferred sequences for the 3' overhang fragment are "TT" (where T represents deoxythymidine) or "UU" (where U represents uracil). Equally advantageously, both complementary strands of a siRNA according to the invention comprise a 3' overhang fragment. In this case, the length and the sequence of the two 3' overhang fragments can be identical or different. Advantageously, both complementary strands of a siRNA according to the invention each comprise the same 3' overhang fragment of 2 nucleotides with the sequence "TT". Such siRNAs comprising the RNA sequences corresponding to SEQ ID NO:2, SEQ ID NO:3, or SEQ ID NO:4 with a "TT" sequence 3' overhang fragment on each strand are shown in FIG. 1C and correspond to advantageous embodiments of the invention. They correspond:

to siRNA MyoVa n°:1 comprising the RNA sequence of the gene sequence SEQ ID NO:2 the strands of which have the specific sequences:

sense strand:    5'-UGACCCUAAGAAGUAUCAATT-3'    (SEQ ID NO: 9)

antisense strand:    5'-UUGAUACUUCUUAGGGUCATT-3';    (SEQ ID NO: 10)

to siRNA MyoVa n°:2 comprising the RNA sequence of the gene sequence SEQ ID NO:3 the strands of which have the specific sequences:

sense strand:    5'-GUAUCAAUCAUAUCGGAUUTT-3'    (SEQ ID NO: 11)

antisense strand:    5'-AAUCCGAUAUGAUUGAUACTT-3';    (SEQ ID NO: 12)

to siRNA MyoVa n°:3 comprising the RNA sequence of the gene sequence SEQ ID NO:4 the strands of which have the sequences:

sense strand:    5'-UCAUAUCGGAUUUCCCUUUTT-3'    (SEQ ID NO: 13)

antisense strand:    5'-AAAGGGAAAUCCGAUAUGATT-3'.    [SEQ ID N° 14]

When a siRNA according to the invention is a shRNA consisting of a single molecule of single stranded RNA in which two complementary portions are paired by Watson-Crick bonds and are linked covalently on one side by a hairpin type structure, that is to say when the siRNA according to the invention is a shRNA, said shRNA preferably comprises or consists of the following sequence:

5'-GUAUCAAUCAUAUCGGAUUCUCAA-GAGAAAUCCGAUAUGAUUGAU AC-3' (SEQ ID NO:17), wherein the portions in bold correspond to the two complementary portions paired by Watson-Crick bonds, corresponding to the RNA with the gene sequence SEQ ID NO:3 comprised in the sense strand of siRNA MyoVa n°:2 and its complementary sequence, and the portion not in bold corresponds to the sequence with the hairpin structure linking the two complementary strands.

Furthermore, in a siRNA according to the invention, the sense RNA strand and/or the antisense RNA strand can also comprise at least one chemical modification in their sugar portions, their nucleobase portions or their internucleotide backbone. Such modifications can notably make it possible to inhibit the breakdown of siRNAs by nucleases in vivo. All chemical modifications that enable the improvement of the stability and in vivo bioavailability of siRNAs according to the invention are thus included in the scope of the invention. Among the advantageous modifications to the sugar portions, mention can be made notably of modifications taking place in position 2' of ribose, such as 2'-deoxy, 2'-fluoro, 2'-amino, 2'-thio, or 2'-O-alkyl, and particularly 2'-O-methyl, replacing the normal 2'-OH groups on the ribonucleotides, or the presence of a methylene bridge between positions 2' and 4' of ribose (LNA). Concerning nucleobases, it is possible to use modified bases, such as notably 5-bromo-uridine, 5-iodo-uridine, $N^3$-methyl-uridine, 2,6-diaminopurine (DAP), 5-methyl-2'-deoxyCytidine, 5-(1-propynyl)-2'-deoxy-Uridine (pdU), 5-(1-propynyl)-2'-deoxyCytidine (pdC), or bases conjugated with cholesterol. Lastly, advantageous modifications of the internucleotide backbone include replacing the phosphodiester groups in the backbone by phosphorothioate, methylphosphonate, phosphorodiamidate groups, or using a backbone composed of N-(2-aminoethyl)-glycine units linked by peptide bonds (PNA, Peptide Nucleic Acid). The various modifications (base, sugar, backbone) can obviously be combined to give modified nucleic acids of the morpholino type (bases fixed to a morpholine ring and linked by phosphorodiamidate groups) or PNA (bases fixed to N-(2-aminoethyl)-glycine units linked by peptide bonds).

SiRNAs according to the invention are "isolated", which means that they are not in a natural state but have been obtained by any means involving human intervention. Notably, siRNAs according to the invention can have been obtained by purification of siRNAs that already exist, by chemical synthesis, by amplification of the desired nucleotide sequences by a polymerase chain reaction (PCR), or by recombinant synthesis. Many companies also offer customised siRNA synthesis, notably companies such as Eurogentec, Ambion, Dharmacon, or Qiagen.

The invention also relates to siRNAs according to the invention, for use as a cosmetic agent. The expression "cosmetic agent" as used herein is understood to mean a substance that makes it possible to maintain or improve the aesthetic appearance of an external part of the human or animal body.

The invention further relates to siRNAs according to the invention, for use as drugs. Indeed, siRNAs according to the invention are novel as drugs.

Another object of the invention is a composition comprising at least one siRNA according to the invention and an acceptable carrier. The term "acceptable carrier" as used herein is understood to mean any cosmetologically or pharmacologically acceptable carrier known to those skilled in the art.

A composition according to the invention is intended for cosmetic and/or therapeutic treatment of the skin and is thus advantageously administered topically.

A composition for topical application according to the invention can be formulated in any galenic form habitually used for topical application, such as for example in the form of an aqueous solution, a white or coloured cream, an ointment, a milk, a lotion, a gel, a salve, a serum, a paste, an oil in water or water in oil emulsion, or a foam. It is possible to apply it to the skin in an aerosol form. It can also be presented in the form of a solid, either powdery or not, for example in the form of a stick. It can also be presented in the form of patches, pencils, brushes and applicators for localised application on marks on the face or hands.

A composition according to the invention can further comprise any kind of vehicle known to those skilled in the art making it possible to improve the delivery and the bioavailability of siRNAs according to the invention. Particular vehicles that can be used with siRNAs comprise notably liposomes and peptides able to cross the cell membrane (known as CPP for "Cell-Permeable Peptides"). The term "liposome" as used herein is understood to mean an artificial lipid vesicle with a membrane consisting of one or several lipid bilayers and which has the ability to encapsulate and protect proteins and nucleic acids and fuse with the cell membrane, thus allowing it to deliver the encapsulated product inside the cell. Thus the use of liposomes makes it possible to protect the siRNAs and facilitate their penetration into cells. The expression CPP as used herein is understood to mean peptides able to be internalised and then reach the cytoplasmic and/or nuclear compartments of living cells. Examples of such CPPs include the peptides Penetratine, Transportan, Tat, MAP and SynB1. Some particularly useful examples of CPPs consist of amphipathic peptides derived from viruses which interact directly with nucleic acids to be delivered in order to form nanoparticles that can diffuse through the plasma membrane. Conjugating siRNAs according to the invention to any CPP can thus also make it possible to protect siRNAs and facilitate their entry into cells in vivo.

A composition according to the invention can also comprise one or several actives aiming to increase the desired effects. In a particular embodiment, a composition according to the invention can further notably comprise at least one other depigmenting agent. The expression "depigmenting agent" as used herein is understood to mean any substance which acts directly on the melanocytes by inhibiting their activity, or one of the steps of the melanin synthesis pathway, or else the transport of melanosomes to the dendrites and their transfer to the keratinocytes. Among known depigmenting agents suitable to be added to a composition according to the invention, mention can notably be made of hydroquinone and its derivatives, retinol or tretinoin, ascorbic acid and its derivatives, placenta extracts, kojic acid, ferulic acid, arbutin, dihydroxybenzene derivatives, (WO 00/47045), guaiacol derivatives (WO00/47179), 4-(2,3-dihydroxyphenyl)-cyclohexanol (WO 00/56279), resorcinol derivatives (WO 00/56702), phenolic amides (WO 99/32077). Other depigmenting agents suitable for adding to a composition according to the invention comprise antisense oligonucleotides or siRNAs directed against genes other than the one coding for myosin Va protein involved in a step of the melanin synthesis pathway or in the transport of melanosomes to the dendrites and their transfer to the keratinocytes, such as notably antisense oligonucleotides or siRNA targeting tyrosinase (see WO 01/58918 and WO 2005/060536), the protein TRP-1 (see WO 01/58918) or the protein PKC β1 (see WO 2005/073243).

Compositions according to the invention can also comprise active substances or excipients habitually used in topical compositions directed towards skin care such as for example chemical and physical sun filters (such as for example octyl methoxycinnamate, butyl-methoxydibenzoyl-methane, titanium oxide and zinc oxide), antiglycation agents and/or antioxidants taken separately or in combination (such as for example tocopherol and its derivatives, ergothioneine, thiotaurine, hypotaurine, aminoguanidine, thiamine pyrophosphate, pyridoxamine, lysine, histidine, arginine, phenylalanine, pyridoxine, adenosine triphosphate), anti-inflammatory agents (such as for example stearylglycyrrhetinate), soothing agents and their mixtures, preserving agents (anti-bacterial or anti-fungal), moisturising agents, pH modifiers, keratolytic and/or desquamating agents (such as for example salicylic acid and its derivatives), vitamins, thickeners, emollients, spa water, tensioactives, polymers, silicone oils, plant oils, essential oils, fragrances, colorants or pigments, etc.

The invention also relates to the use of at least one siRNA or of a composition according to the invention as a cosmetic agent for depigmenting or bleaching the skin. SiRNAs and compositions according to the invention can be used as cosmetic agents for the depigmentation or bleaching of the skin, either overall in order to decrease the pigmentation of all the whole skin, or in hyperpigmented areas, whatever the origin of the hyperpigmentation of said areas. This is because such use makes it possible to make the pigmentation of the skin more even, thus improving its appearance. Moreover, even in the absence of hyperpigmented areas, some people may want a lighter overall pigmentation, which can be obtained by a cosmetic use according to the invention.

The invention further relates to the use of at least one siRNA or of a composition according to the invention for manufacturing a drug intended to the treatment or prevention of skin hyperpigmentation of the skin, in particular epidermal hyperpigmentation, melasmas and post-inflammatory hyperpigmentations. The hyperpigmentation can originate from many different disorders. Notably mention can be made of melanoses of the face and neck, such as chloasma, Riehl's melanosis, Reticulated Pigmentary Poikilodermia of the Face and Neck, or hereditary sclerosing poikilodermia; freckles; café-au-lait spots; Sutton's naevus; hyperpigmentations from metabolic causes such as haemochromatosis, Addison's disease, Cushing's syndrome or hyperthyreosis; and hyperpigmentation due to exogenous causes such as hyperpigmentations caused by drugs (substances such as chlorpromazine, phenotiazines, hydantoin, inorganic arsenic, antimalarials) or heavy metals (silver, gold, mercury); post-inflammatory hyperpigmentations induced after trauma, eczema rashes, chronic lichen simplex, lupus erythematosus, and dermatoses including pytyriasis rosea, psoriasis, dermatitis herpetiformis, fixed pigmented erythema, and photo-dermatitis; Rothmund-Thomson syndrome; benign acanthosis nigricans or malignant acanthosis nigricans. The use of a siRNA or of a composition according to the invention for producing a drug makes it possible to treat these different pathologies and make the areas of hyperpigmentation resulting from these disorders disappear. It also makes it possible to prevent the appearance of areas of hyperpigmentation resulting from these different disorders.

The invention also relates to a method of cosmetic treatment for depigmentation and bleaching of the skin, comprising the topical administration of a composition according to the invention.

The invention further relates to a method of therapeutic treatment of skin hyperpigmentation, comprising the topical administration of a composition according to the invention.

The following examples illustrate the present invention without limiting it in any way.

DESCRIPTION OF THE DRAWINGS

FIG. 1. Design of 3 siRNAs targeting exon F in human myosin Va protein. A. Nucleotide coding sequence of the transcripts of human myosin Va protein comprising exon F (includes exons ADCDEF) (SEQ ID NO: 21). The portion corresponding to exon F is underlined (SEQ ID NO: 1). B. Detail of the sequence of exon F (SEQ ID NO: 1). The positions corresponding to the three siRNAs selected are either underlined (siRNA MyoVa n°:2 (SEQ ID NO:3)) or overlined (siRNA MyoVa n°:1 (SEQ ID NO:2), and MyoVa n°:3 (SEQ ID NO:4)). C. Structure of the 3 siRNAs (SEQ ID NOS: 9-14) targeting exon F in the human myosin Va protein.

EXAMPLES

Example 1

Figure 2:
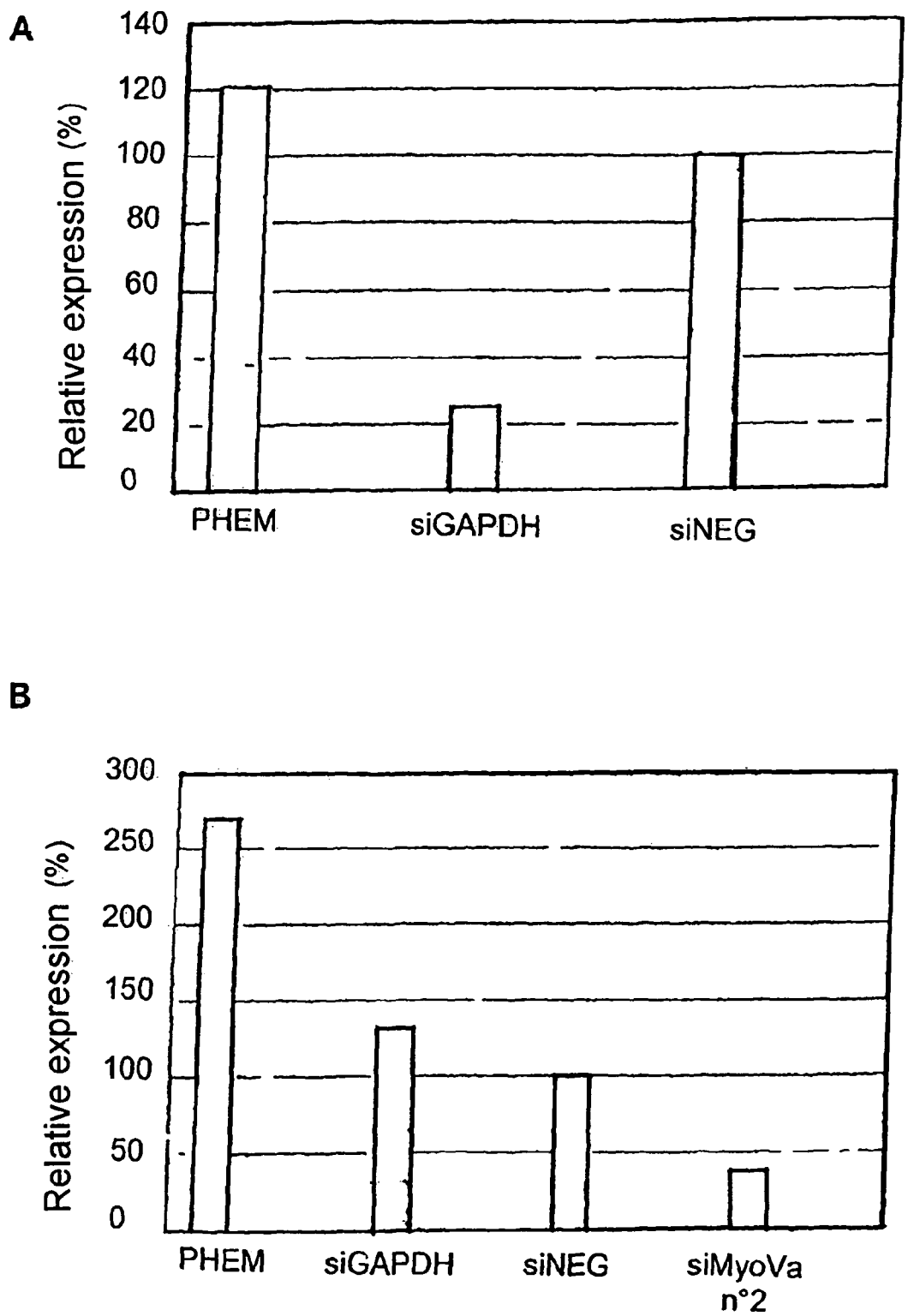
FIG. 2. Decrease in the quantity of transcripts of the myosin Va protein comprising exon F in PHEM cells electroporated with 2 µM of siRNA MyoVa n°:2 (SEQ ID NO:3). PHEM cells were electroporated with 2 µM of negative control siRNA, siRNA targeting the GAPDH gene or siRNA MyoVa n°:2 (SEQ ID NO:3). The effect of the different siRNAs was measured at the RNA level by QPCR. A. Relative expression level of the GAPDH gene as a function of the electroporated siRNA. B. Expression level of transcripts of the myosin Va protein comprising exon F as a function of the electroporated siRNA.

Design, Synthesis and Study of 3 siRNAs Targeting Exon F of the Human Myosin Va Protein 1.1 Design and Synthesis of 3 siRNAs The sequence of the splicing variant of human myosin Va protein comprising exon F (in fact comprises exons ABCDEF) is shown in FIG. 1A.

Within exon F, three siRNAs targeting exon F of the human myosin Va protein were designed and synthesised using the siRNA design and synthesis service from Eurogentec. The portions of exon F for which theses siRNAs are specific are indicated in FIG. 1B.

The three siRNAs were synthesised with 3' overhang fragments having the sequence "TT", as shown in FIG. 1C. These three siRNAs are hereinafter referred to as MyoVa n°:1 (sense strand comprises SEQ ID NO:2), MyoVa n°:2 (sense strand comprises SEQ ID NO:3), or MyoVa n°:3 (sense strand comprises SEQ ID NO:4), the SEQ ID number shown in brackets corresponds to the sequence of the fragment of exon F of the human myosin Va protein comprised in the sense RNA strand of the siRNA.

1.2 Test of siRNA Efficacy after Electroporation into Primary Human Epidermal Melanocytes (PHEM)

1.2.1 Choice of Electroporation Programme

Primary human epidermal melanocytes (PHEM) were grown in Ham's F10 medium (Gibco, Invitrogen Ltd, Paisley, UK) supplemented with 2.5% foetal calf serum (FCS), 1% Ultroser, 5 ng/ml of basic fibroblast growth factor (bFGF), 10 ng/ml of endothelin-1 (ET-1), 0.33 nM of choleric toxin (CT), 0.033 mM of isobutyl-methyl-xanthine (IBMX) and 5.3 nM of 12-O-tetradecanoyl phorbol-13-acetate (TPA). The cells were grown to a confluence of 40-70% and used between passages 2 and 5.

In the first instance, the plasmid pMAX-GFP (3 μg) was used to test three different programmes for electroporation of the melanocytes, namely programmes U16, U20 and U24. 500 000 cells were used for electroporation. The NHEM-Neo Nucleofector kit (Amaxa, #VDP-1 003) for normal-Neonatal human epidermal melanocytes was used for all electroporations.

The electroporated cells in T25 flasks were evaluated alive at 24-48 hours under an Arcturus microscope (LCM) fitted with a fluorescent filter able to detect green fluorescence signals emitted by the pMAX-GFP plasmid.

The electroporated cells were also grown on glass slides. 24 hours after electroporation, the cells were fixed in iced methanol and mounted on glass slides with mounting fluid (DAKO). The cells involved in expressing green fluorescence signals were analysed under a Zeiss fluorescence microscope.

The results obtained with living cells showed that an equal quantity of dead cells was observed whatever the electroporation programme, but that the most effective electroporation is obtained with the U24 programme. The results obtained with the fixed cells confirmed that the U24 programme gives the most effective electroporation. Therefore the U24 programme was used thereafter in all the other experiments.

1.2.2 Preliminary Analysis of the Efficacy of siRNA MyoVa n°:2 (SEQ ID NO:3)

500 000 PHEM cells were electroporated with pMAX-GFP (3 μg) plasmid and the following siRNA duplexes: a positive control targeting the FAM labelled GAPDH (3 μg or 2 μM, Ambion), a negative control BLOCK-iT™ Fluorescent Oligo (Invitrogen), and the duplex of siRNA MyoVa n°:2 (SEQ ID NO:3) specific for exon F of the gene for human myosin Va protein. The U24 programme was used for electroporation and the cells were harvested 24 hours after electroporation.

The analysis was then carried out on the RNA by real time quantitative RT-PCR (QPCR). Briefly, after extraction of the RNA, the samples were treated with DNase and the cDNA was synthesised using iScript reverse transcriptase (Biorad). The QPCR primers for exon F of the myosin Va protein (sense primer: 5' CAGCCTGCAGCACGAGATC 3', SEQ ID NO:5, antisense primer: 5' TCTTAGGGTCATCTGCATATAAT-TCCT 3', SEQ ID NO:6) and the GAPDH were designed using the PrimerExpress 2.0 software (Applied Biosystems) with the Taqman parameters as default, modifying only the minimum size limit for the amplicon (75 bp). The relative levels of gene expression were determined using an SYBR green|RT-PCR test in two optimised steps. The Ct comparison method was used for quantification. The PCR reactions were carried out in an ABI Prism 7000 Sequence Detection System (Applied Biosystem). In order to correct for the differences in the amount of RNA extracted and in the efficacy of cDNA synthesis, the relative levels of gene expression were standardised against the geometrical mean of three housekeeping genes (RPL13a, SDHA et UBC) which had already been used for melanocyte analysis (Vandesompele J et al. Genome Biol.: 3: research0034.001-research0034.001, 2002).

The results obtained show that the siRNAs used lead to a reduction in the expression of RNA by the target genes after electroporation in PHEM cells. In fact, a 75% reduction for GAPDH (FIG. 2A) and 62% for transcripts of the myosin Va protein comprising exon F (FIG. 2B) was observed compared with the negative control.

1.2.3 Expression of the Transcripts of the Myosin Va Protein Gene in PHEM Cells after Electroporation with siRNAs MyoVa n°:1 (SEQ ID NO:2), MyoVa n°:2 (SEQ ID NO:3), or MyoVa n°:3 (SEQ ID NO:4)

500 000 PHEM cells were electroporated with Nucleofector reagent (MOCK) alone, the siRNA targeting GAPDH (1 μM), a negative control siRNA, or one of the three siRNAs MyoVa n°:1 (SEQ ID NO:2), MyoVa n°:2 (SEQ ID NO:3), or MyoVa n°:3 (SEQ ID NO:4) specific for exon F of the gene for myosin Va protein. The U24 programme was used for electroporation and the cells were harvested 48 hours after electroporation.

The analysis was then carried out on the RNA by QPCR as previously described for the transcripts comprising exon F (exon F detection) or for all the transcripts by detecting the globular portion (GP) of myosin Va protein. The QPCR primers for the globular portion (GP) of the myosin Va protein (sense primer: 5' GCAGTCAATTTGATTCCAGGATT 3', SEQ ID NO:7; antisense primer: 5' TGATCATCATTCAGG-TAGTCAGCAT 3', SEQ ID NO:8) were designed using the PrimerExpress 2.0 (Applied Biosystems) software, as previously described.

Figure 3:
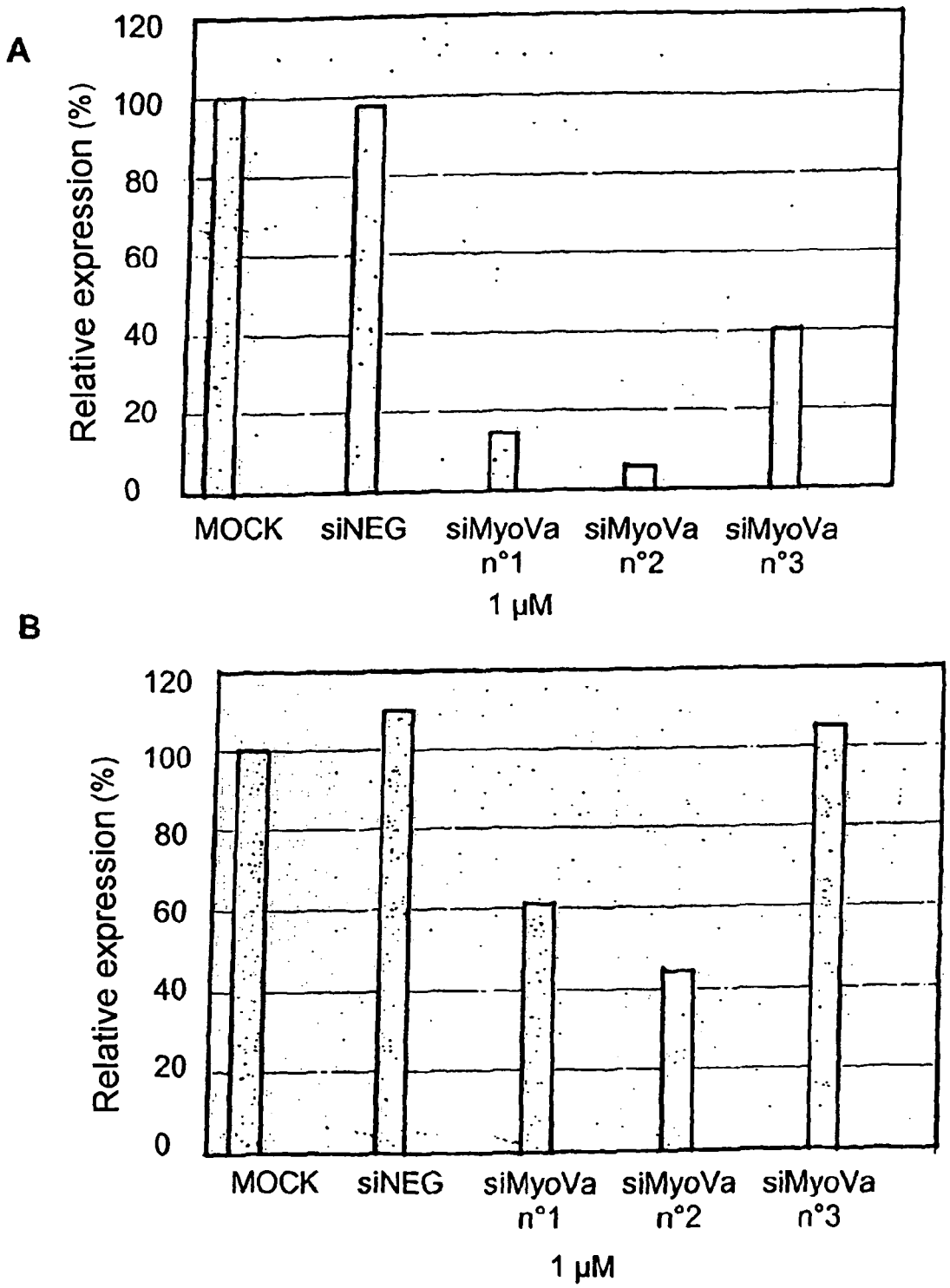
FIG. 3. Specific reduction in the quantity of transcripts of the myosin Va protein comprising exon F, but not the transcripts not comprising exon F. A. Relative expression level of transcripts of the myosin Va protein comprising exon F as a function of the electroporated siRNA. B. Relative expression level of all transcripts of the myosin Va protein by detection of the globular portion (GP) as a function of the electroporated siRNA.

For the transcripts comprising exon F of myosin Va protein, inhibitions of 85%, 94% and 60% were observed for the siRNAs MyoVa n°:1 (SEQ ID NO:2), MyoVa n°:2 (SEQ ID NO:3), and MyoVa n°:3 (SEQ ID NO:4) respectively (FIG. 3A). Thus maximum inhibition was obtained with the siRNA MyoVa n°:2 (SEQ ID NO:3).

As for all the transcripts of myosin Va protein, detected using the globular portion (GP), inhibitions of 39%, 56% and 0% were observed for the siRNAs MyoVa n°:1 (SEQ ID NO:2), MyoVa n°:2 (SEQ ID NO:3), and MyoVa n°:3 (SEQ ID NO:4) respectively (FIG. 3B). This reduced inhibition can be explained notably by the fact that the siRNAs used specifically target exon F and so do not result in the breakdown of transcripts not comprising exon F.

1.2.4 Conclusions

These first results show clearly that it is possible to reduce specifically and significantly the quantity of transcripts of the human myosin Va protein comprising exon F by using the three synthesised siRNAs, without affecting the transcripts that do not comprise exon F.

The most significant results were obtained with siRNA MyoVa n°:2 (SEQ ID NO:3).

1.3 Optimisation of siRNA Concentration 1.3.1 Determination of a Minimum Concentration with Maximum Efficacy With the aim of determining the minimum siRNA concentration for maximum efficacy, different concentrations ranging from 0.05 to 2 μM were tested using the same protocol as previously described. The negative control siRNA and the siRNA targeting GAPDH were used at a concentration of 1 μM.

The U24 programme was used and the cells were analysed 48 hours after electroporation.

The analysis was then carried out on the transcripts comprising exon F (specific exon F detection) by QPCR as previously described.

Figure 4:
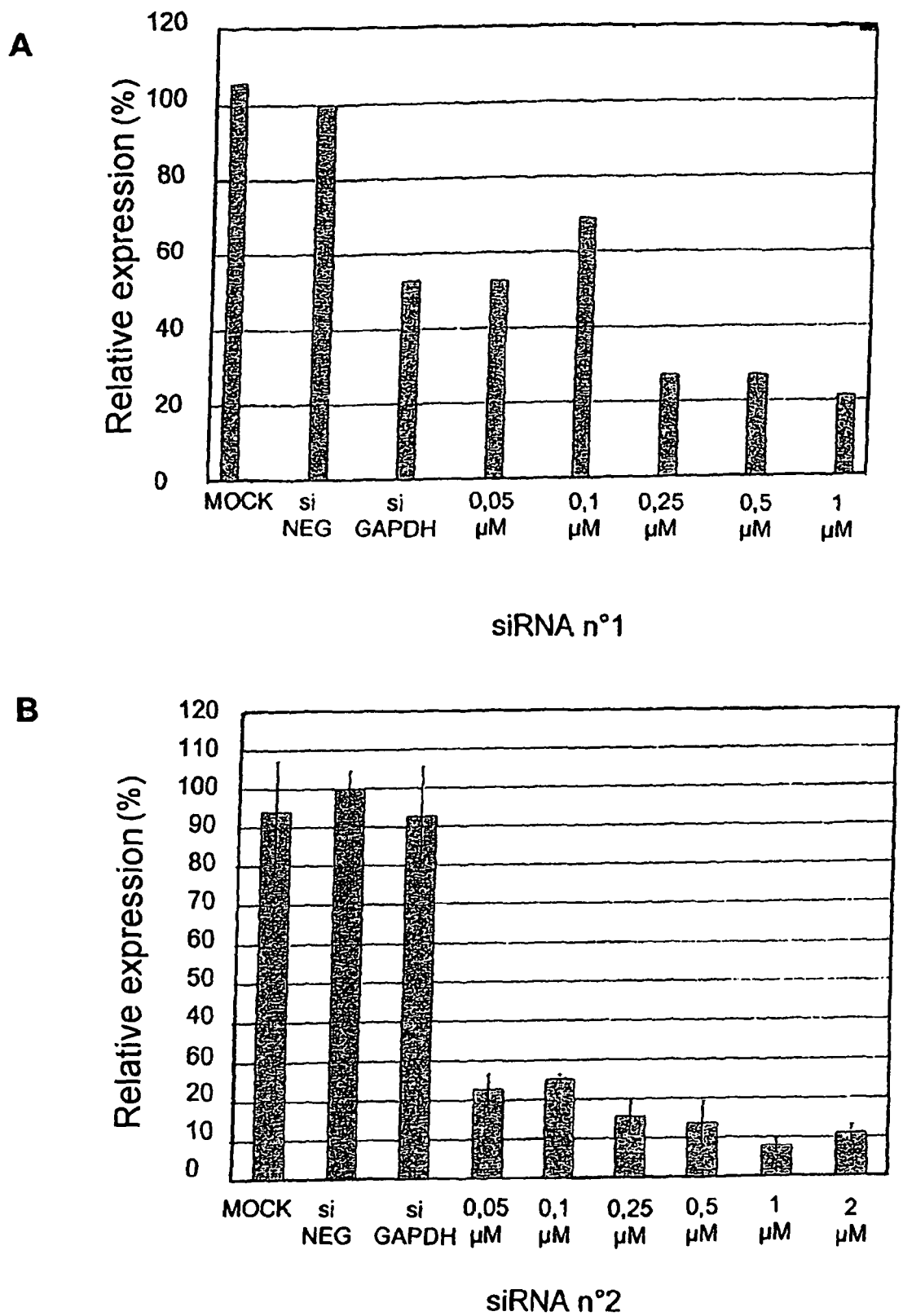
FIG. 4. Determination of the minimum concentration having maximum efficacy for the siRNAs MyoVa n°:1 (SEQ ID NO:2) and MyoVa n°:2 (SEQ ID NO:3). Different concentrations of siRNAs targeting exon F of human myosin Va protein were tested for the siRNAs A. MyoVa n°:1 (SEQ ID NO:2) and B. MyoVa n°:2 (SEQ ID NO:3). For MyoVa n°:2, the results are shown in the form of means with standard deviation.

For siRNA MyoVa n°:1 (SEQ ID NO:2), a reduction in transcripts comprising exon F, as compared to the negative control, of 47.5%, 31%, 73%, 73%, and 79% was observed for concentrations of 0.05; 0.1; 0.25; 0.5 and 1 μM respectively (FIG. 4A). The greatest effect is thus obtained with a concentration of 1 μM, but almost equally effective inhibition is obtained with concentrations of 0.25 and 0.5 μM.

As far as the siRNA MyoVa n°:2 (SEQ ID NO:3) is concerned, a large reduction was observed at all concentrations tested (FIG. 4B). Maximum effect was observed for a concentration of 1 µM, but the inhibition obtained with a concentration of 0.5 µM was almost as great.

Therefore an optimum siRNA concentration is around 0.5-1 µM.

1.3.2 Influence of siRNA Concentration on Cell Viability

The influence of siRNA concentration on cell viability was then analysed using siRNA MyoVa n°:2 (SEQ ID NO:3). To this end, the same range of concentrations (0.05 to 2 µM) was tested in parallel with an MTS test (Promega Benelux) which determines the number of viable cells. The cells were analysed 48 hours after electroporation using the U24 programme.

Figure 5:
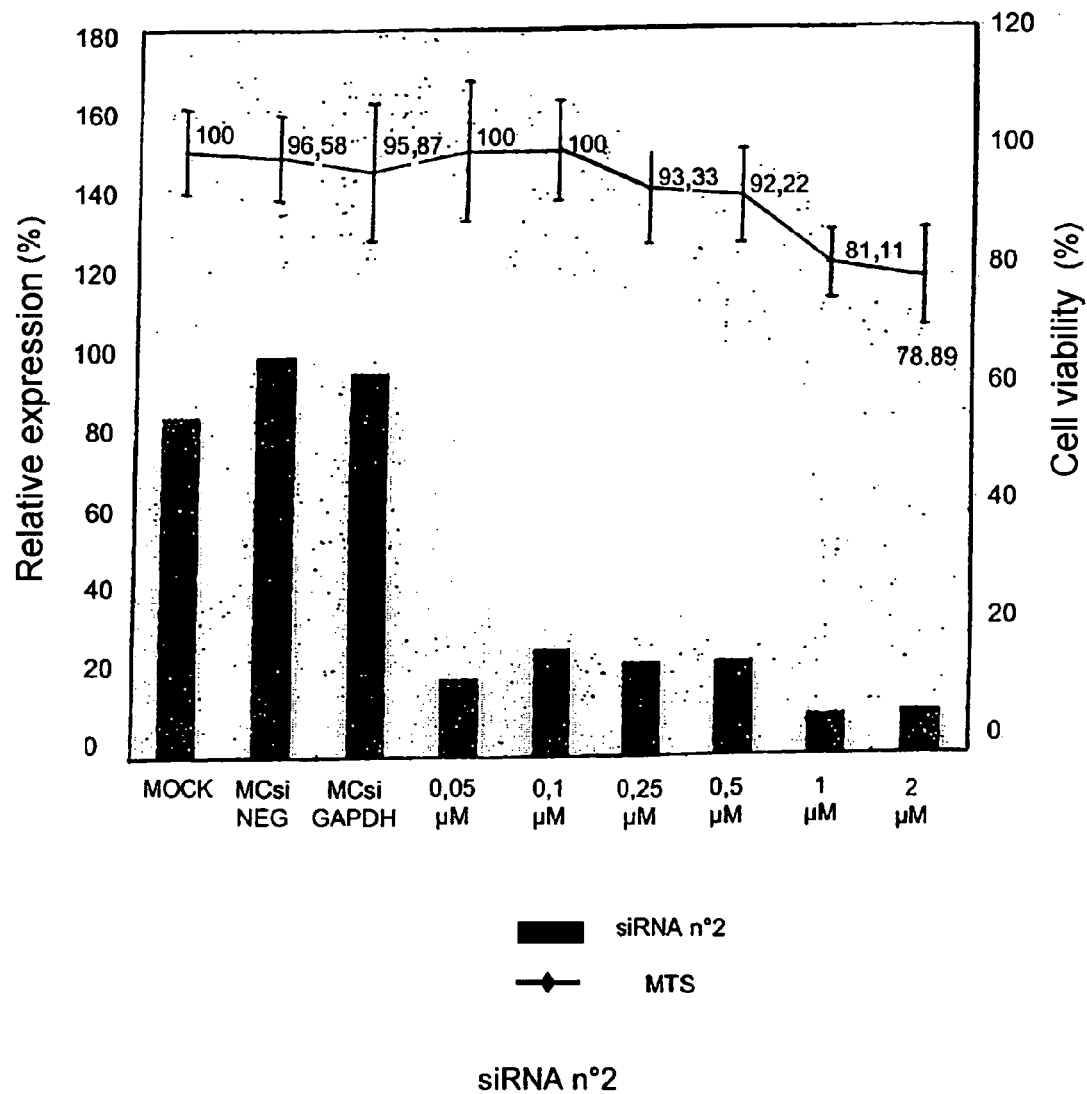
FIG. 5. Effect of siRNA concentration on cell viability. Relative expression level of transcripts comprising exon F and cell viability were determined in parallel for different concentration of siRNA MyoVa n°:2 (SEQ ID NO:3). SiRNA concentrations are given on the X-axis, the relative expression level of transcripts comprising exon F and the cell viability on the Y-axis, as respectively a histogram (grey blocks) and a line showing the mean and standard deviation.

The results are given in FIG. 5 and show that the cell viability is only significantly reduced (about 20%) for siRNA concentrations of 1 or 2 µM. Below 1 µM, cell viability is greater than 90%.

1.3.3 Conclusions

These results show that the effect of siRNAs targeting exon F of myosin Va protein is dose-dependent, and that maximum effect can be obtained for a concentration comprised between 0.5 and 1 µM.

Moreover, below 1 µM, the presence of siRNAs does not affect the viability of the PHEM cells.

A concentration of 0.5 µM therefore seems best, because this combines high efficacy and high cell viability. This concentration was used in all the following experiments described below.

1.4 Analysis Over Time

In order to analyse the effect over time of siRNAs according to the invention, PHEM cells electroporated with 0.5 µM of siRNA MyoVa n°:1 (SEQ ID NO:2) or MyoVa n°:2 (SEQ ID NO:3) were analysed by QPCR as described above at 24, 48, 72 and 96 hours after electroporation. Cells treated with the positive or negative controls (0.5 µM) were analysed 48 hours after electroporation.

Figure 6:
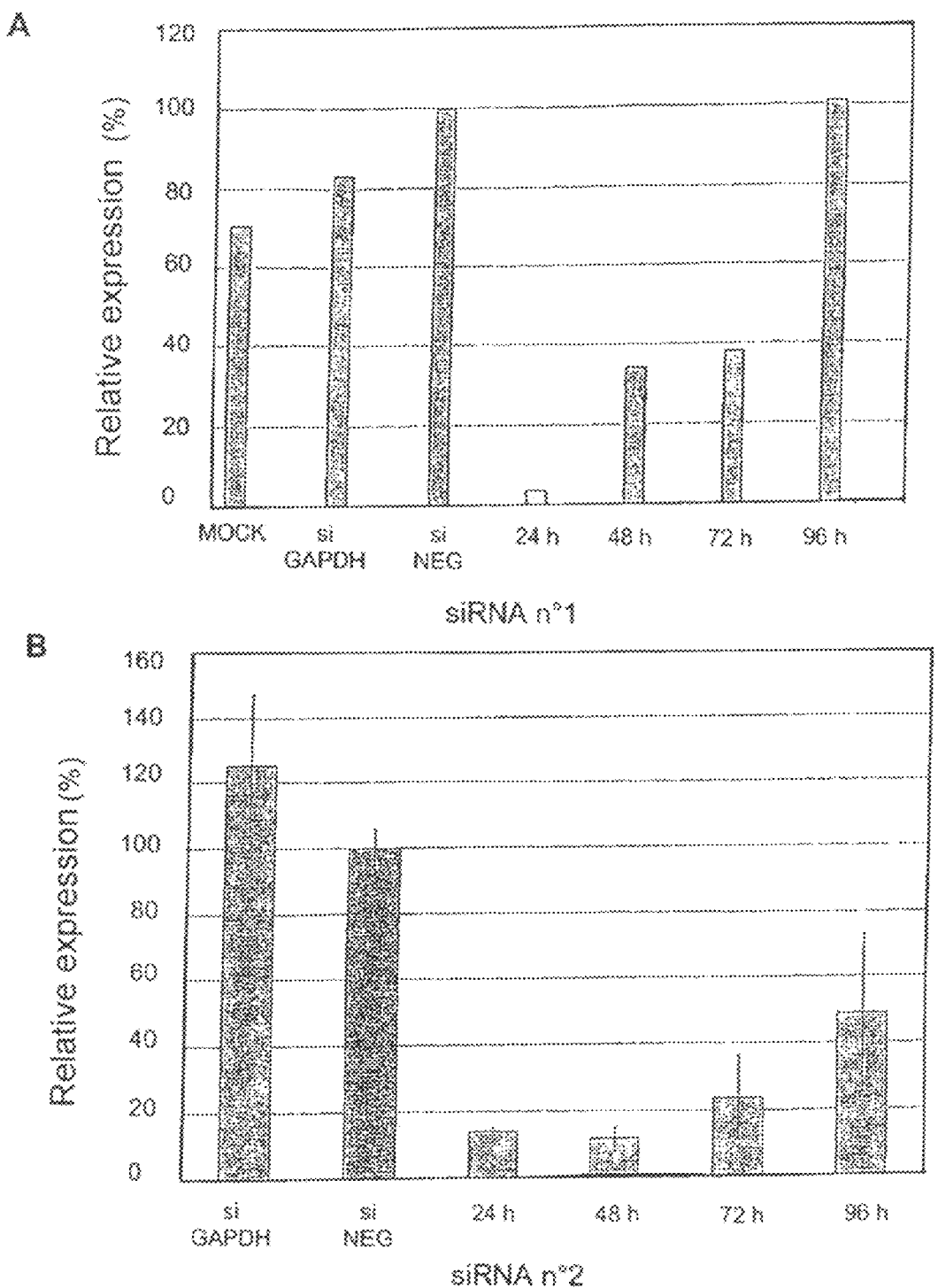
FIG. 6. Efficacy over time of the siRNAs targeting exon F in the human myosin Va protein. The PHEM cells were analysed at different times after electroporation of 0.5 µM of siRNA MyoVa n°:1 (SEQ ID NO:2) or MyoVa n°:2 (SEQ ID NO:3). A. Relative expression level for MyoVa n°:1 (SEQ ID NO:2). B. Relative expression level for MyoVa n°:2 (SEQ ID NO:3).

For siRNA MyoVa n°:1 (SEQ ID NO:2), the reduction of transcripts comprising exon F is maximum at 24 h (over 90%) and then decreases at 48 h (65%) and 72 h (60%), and the expression level returns to normal at 96 h (see FIG. 6A).

For siRNA MyoVa n°:2 (SEQ ID NO:3), a reduction in transcripts of over 85% was observed at 24 and 48 hours, which then decreased at 72 and 96 hours, while remaining significant compared with the negative control (FIG. 6B).

Thus, these results show that the maximum effect is obtained at 24-48 hours after electroporation, and that the efficacy of the MyoVa n°:2 (SEQ ID NO:3) is greater over time than that of the siRNA MyoVa n°:1 (SEQ ID NO:2).

1.5 Conclusions

Thus, the results presented above show clearly that it is possible to reduce significantly the quantity of transcripts of myosin Va protein comprising exon F by using siRNAs targeting said exon F. Three different siRNAs were tested, and each of these siRNAs reduces the quantity of transcripts of the myosin Va protein comprising exon F. SiRNA MyoVa n°:1 (SEQ ID NO:2), and especially siRNA MyoVa n°:2 (SEQ ID NO:3), are particularly effective.

Moreover, the effect of siRNAs targeting exon F of myosin Va protein is dose-dependent and maximum effect can be obtained at a concentration that does not affect cell viability.

The efficacy also varies over time and reaches a maximum 24-48 hours after electroporation.

Example 2

Influence of the Presence of a siRNA Targeting the Exon F of Human Myosin Va Protein on the Transfer of Melanosomes from Melanocytes to Keratinocytes In Vitro

2.1 Principle of the Test

In order to test the influence of siRNAs according to the invention targeting the exon F of human myosin Va protein on the transfer of melanin from melanocytes to keratinocytes, an in vitro test has been developed.

Figure 7:
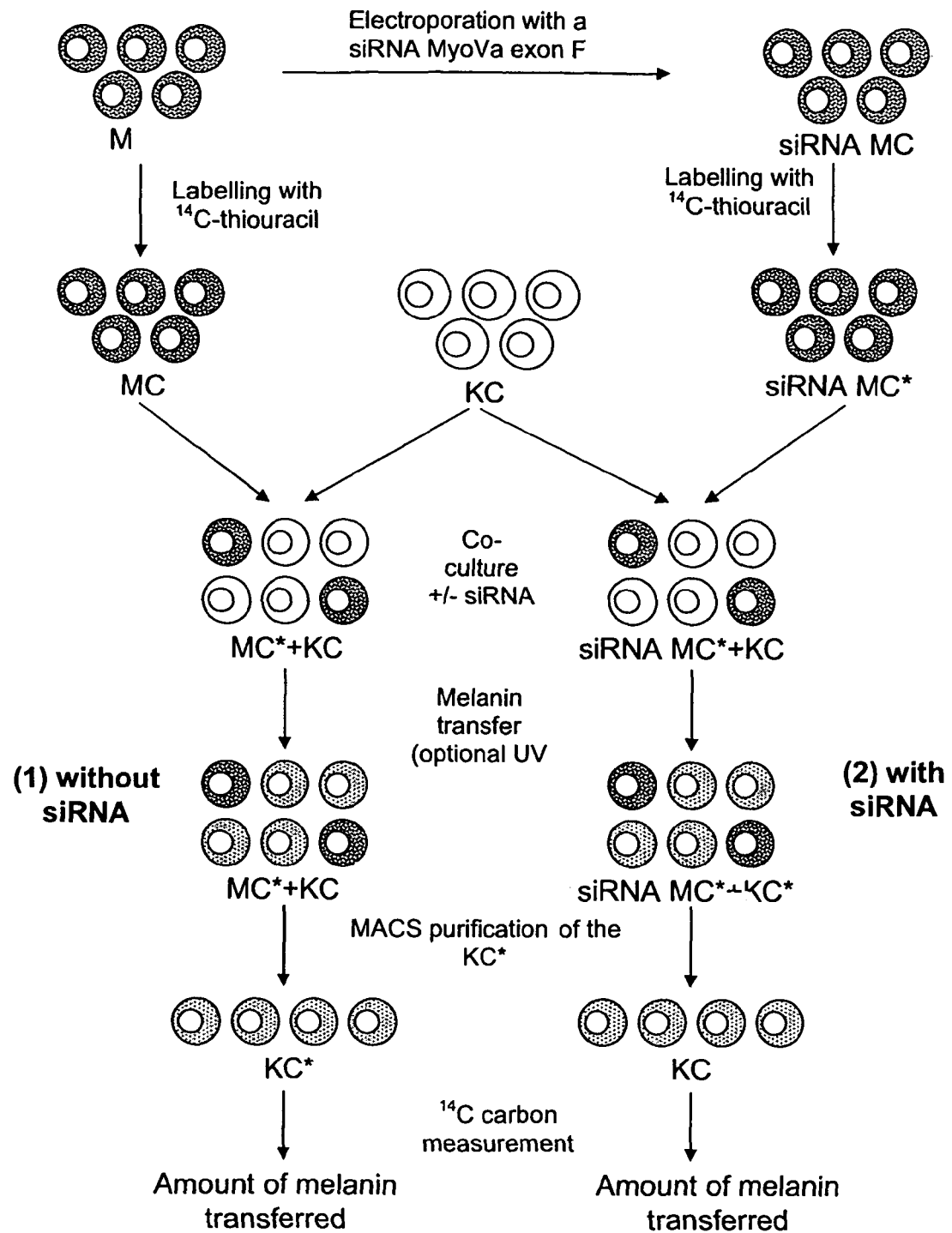
FIG. 7. Principle of the in vitro test of the inhibition of the transfer of melanosomes from melanocytes to keratinocytes by siRNAs targeting the exon F of the human myosin Va protein.

The principle of this test is shown in FIG. 7.

Normal human melanocytes (MC) are electroporated or not with a siRNA targeting exon F of human myosin Va protein at concentrations of 0.1 µM; 0.25 µM; and 0.5 µM. Then, electroporated (siRNA MC) or non electroporated (MC) melanocytes are grown in an enriched TFA medium in the presence of 2[2-14C] thiouracil, which is incorporated in the melanin produced by the MCs, which makes it possible to obtain melanocytes comprising melanin labelled with $^{14}C$ (MC* or siRNA MC*).

MC*s or siRNA MC*s are put into culture in a serum free keratinocytes medium with a low calcium concentration (K-SFM, Gibco) with keratinocytes (KC) which have undergone 1 or 2 passages in this same medium. MC*s or siRNA MC*s and KCs are put into culture at a ratio of 1 to 3.

The co-culture is then optionally irradiated with UV to stimulate the transfer of the melanosomes from the MC*s or the siRNA MC*s to the KCs. This is done because it is known that UV irradiation stimulates the transfer of melanosomes from melanocytes to keratinocytes. After co-culture and optional UV irradiation, keratinocytes are $^{14}C$ radioactive (KC*) in proportion to the quantity of melanin transferred from the MC*s or siRNA MC*s.

Then KC*s are purified by negative selection using MACS technology (Miltenyi Biotech) with an anti-CD117 PE antibody which binds to melanocytes and anti-PE beads.

Lastly, the $^{14}C$ radioactivity of purified KC*s is measured.

2.2 Results

The results obtained show that in the absence of electroporation with a siRNA targeting the exon F of the human myosin Va protein, UV irradiation makes it possible to stimulate effectively the transfer of melanin from the melanocytes to the keratinocytes.

On the contrary, when electroporation is performed with a siRNA targeting the exon F of myosin Va protein, the quantity of $^{14}C$ radioactive melanin transferred to keratinocytes after UV irradiation is reduced as compared to the control without electroporation.

2.3 Conclusions

These results show clearly that the use of siRNA targeting the exon F of myosin Va protein makes it possible to reduce the transfer of melanin from the melanocytes to the keratinocytes, thus validating the strategy used by the inventors to reduce the pigmentation of the skin.

Example 3

Efficacy of siRNAs Targeting the Exon F of the Myosin Va Protein after their Transfection into Primary Human Epidermal Melanocytes (PHEM)

3.1 Transfection of PHEM with siRNAs Targeting the Exon F of the Myosin Va Protein 3.1.1 Optimisation of the Transfection with HiPerFect Transfection Reagents 200 000 PHEM (in 0.5 ml of medium/6 well plate) were transfected with siRNA MyoVa n°:2 (SEQ ID NO:3) and BLOCK-iT™ Fluorescent oligo oligonucleotide (Invitrogen) as a negative control. For each transfection, 25 nM or 10 nM of each siRNA was used in combination with either 12 or 18 μl of HiPerFect reagent (Qiagen).

The evaluation inhibition at RNA level, either simply for the transcripts comprising exon F (MyoVa exF transcripts), or for all transcripts of myosin Va protein detected in the GP part (MyoVa GP transcripts), was measured by quantitative real time PCR as described above in the paragraph Example 1.2.2.

Figure 8A:
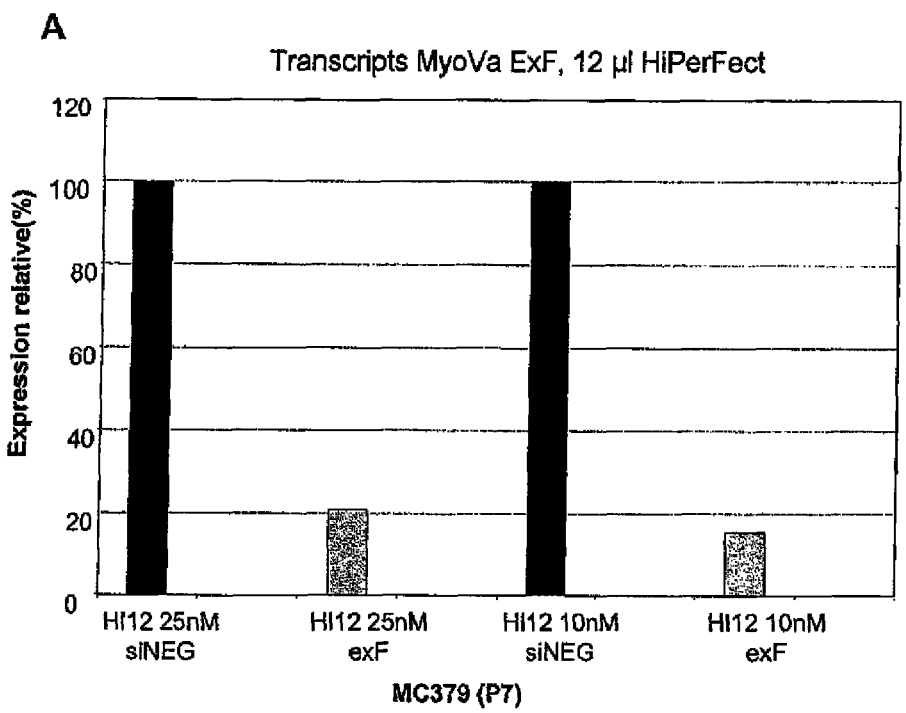
FIG. 8. Evaluation of the inhibition of transcripts comprising exon F (MyoVa exF transcripts) and total transcripts of the myosin Va protein detected at the GP portion (MyoVa GP transcripts) in PHEM transfected with 25 nM or 10 nM of siRNA MyoVa n°:2 (SEQ ID NO:3, exF) or BLOCK-iT™ Fluorescent oligo oligonucleotide (siNEG) and 12 or 18 µl of HiPerFect reagent. A. MyoVa exF transcripts, 12 µl of HiPerFect reagent. B. MyoVa GP transcripts, 12 µl of HiPerFect reagent. C. MyoVa exF transcripts, 18 µl HiPerFect reagent. D. MyoVa GP transcripts, 18 µl of HiPerFect reagent.
Figure 8B:
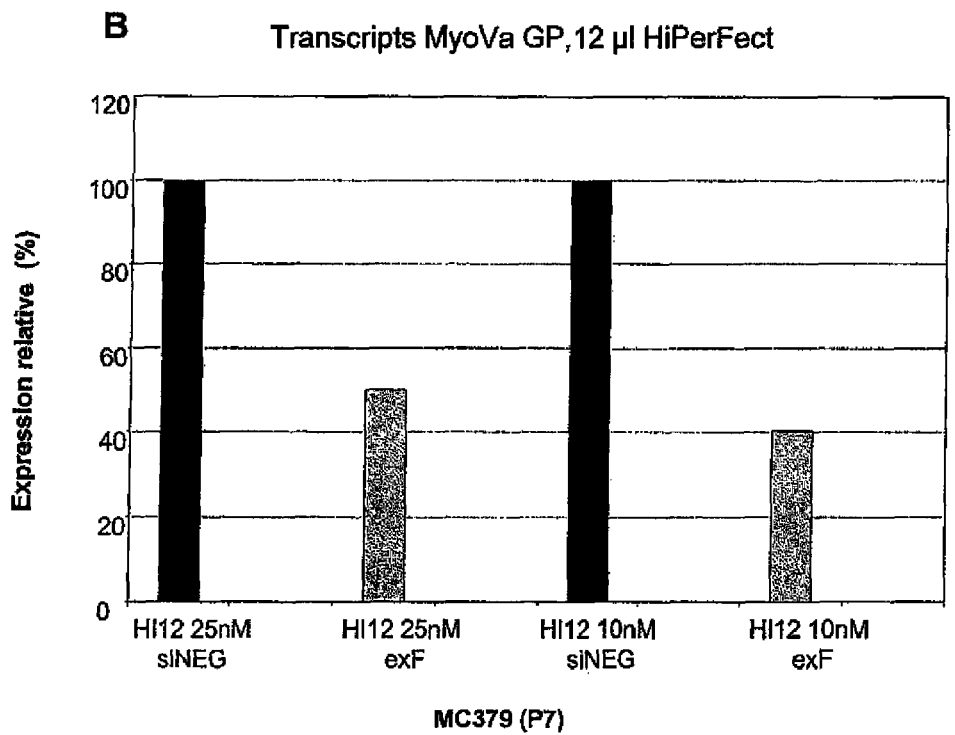
Figure 8C:
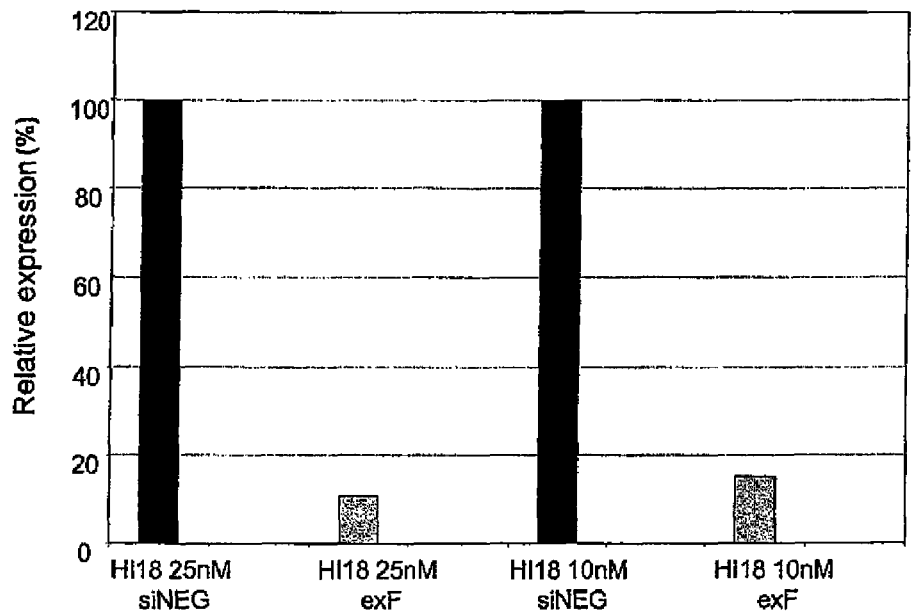
Figure 8D:
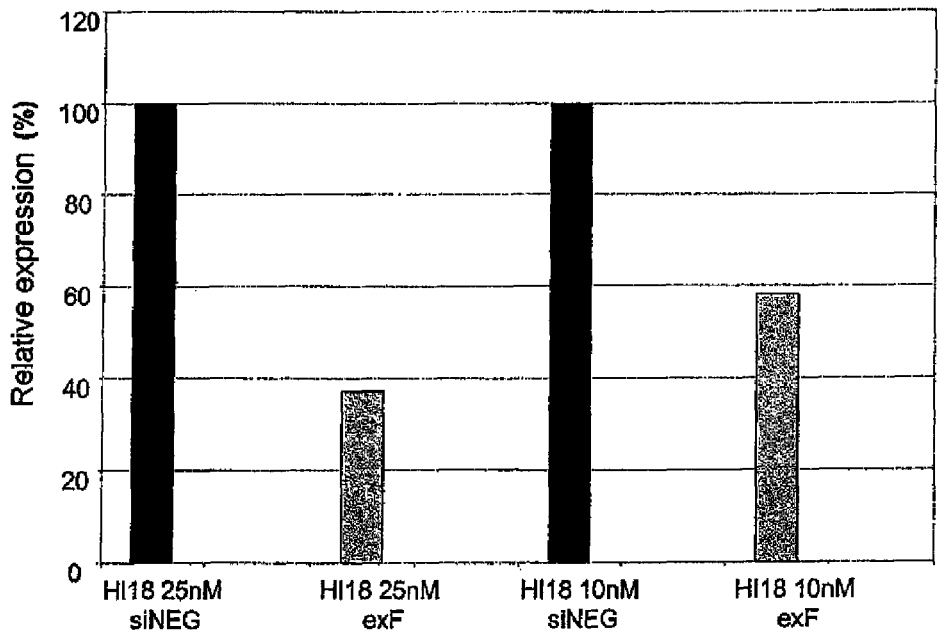

The results obtained with 12 μl or 18 μl of HiPerFect reagent on the MyoVa exF or MyoVa GP transcripts are given in FIG. 8, and show that:
- for MyoVa exF transcripts with 12 μl of HiPerFect reagent, an inhibition of 80% and 85% is observed for 25 nM and 10 nM of MyoVa siRNA n°:2 (SEQ ID NO:3) respectively (FIG. 8A).
- for MyoVa GP transcripts with 12 μl of HiPerFect reagent, an inhibition of 50% and 60% is observed for 25 nM and 10 nM of MyoVa siRNA n°:2 (SEQ ID NO:3) respectively (FIG. 8B).
- for MyoVa exF transcripts with 18 μl of HiPerFect reagent, an inhibition of 90% and 85% is observed for 25 nM and 10 nM of MyoVa siRNA n°:2 (SEQ ID NO:3) respectively (FIG. 8C).
- for MyoVa GP transcripts with 18 μl of HiPerFect reagent, an inhibition of 63% and 58% is observed for 25 nM and 10 nM of MyoVa siRNA n°:2 (SEQ ID NO:3) respectively (FIG. 8D).

3.1.2 Conclusion

These results show a significant and specific inhibition of the number of transcripts of myosin Va protein comprising exon F (MyoVa exF transcripts) by PHEM transfection with MyoVa siRNA n°:2 (SEQ ID NO:3) and HiPerFect reagent. The most effective inhibition is obtained with 25 nM 25 nM of siRNA n°:2 (SEQ ID NO:3), and 18 μl of HiPerFect reagent.

These optimum conditions are used in all the experiments of Example 3 described below.

3.2 Evaluation of the Inhibition Obtained after PHEM Transfection with siRNA MyoVa n°:2 (SEQ ID NO:3).

3.2.1 Evaluation of the Inhibition at RNA Level and Protein Level During a Long Term Experiment 800 000 PHEM (in 2.5 ml of medium/60 well plate) were transfected with 18 μl of HiPerFect reagent and 25 nM of siRNA MyoVa n°:2 (SEQ ID NO:3) or with 25 nM of BLOCK-iT™ Fluorescent oligo oligonucleotide (negative control). The effect of the inhibition was evaluated over a period of 8 days. ⅓ of the cells were used for extracting the RNA and ⅔ of the cells were used to purify the cell lysates.

The evaluation of the inhibition at RNA level for the transcripts comprising exon F (MyoVa exF transcripts) was measured by real time quantitative PCR as described above in the paragraph Example 1.2.2.

In order to correlate the inhibition observed at RNA level with the expression at protein level, a polyclonal antibody directed specifically against the isoforms of the myosin Va protein comprising exon F was developed by Eurogentec. The reactivity and specificity of the purified antibody was tested by Western blot analysis and by immunohistochemistry.

Then the cell lysates obtained during the experiment were analysed by Western blot.

At RNA Level

Figure 9:
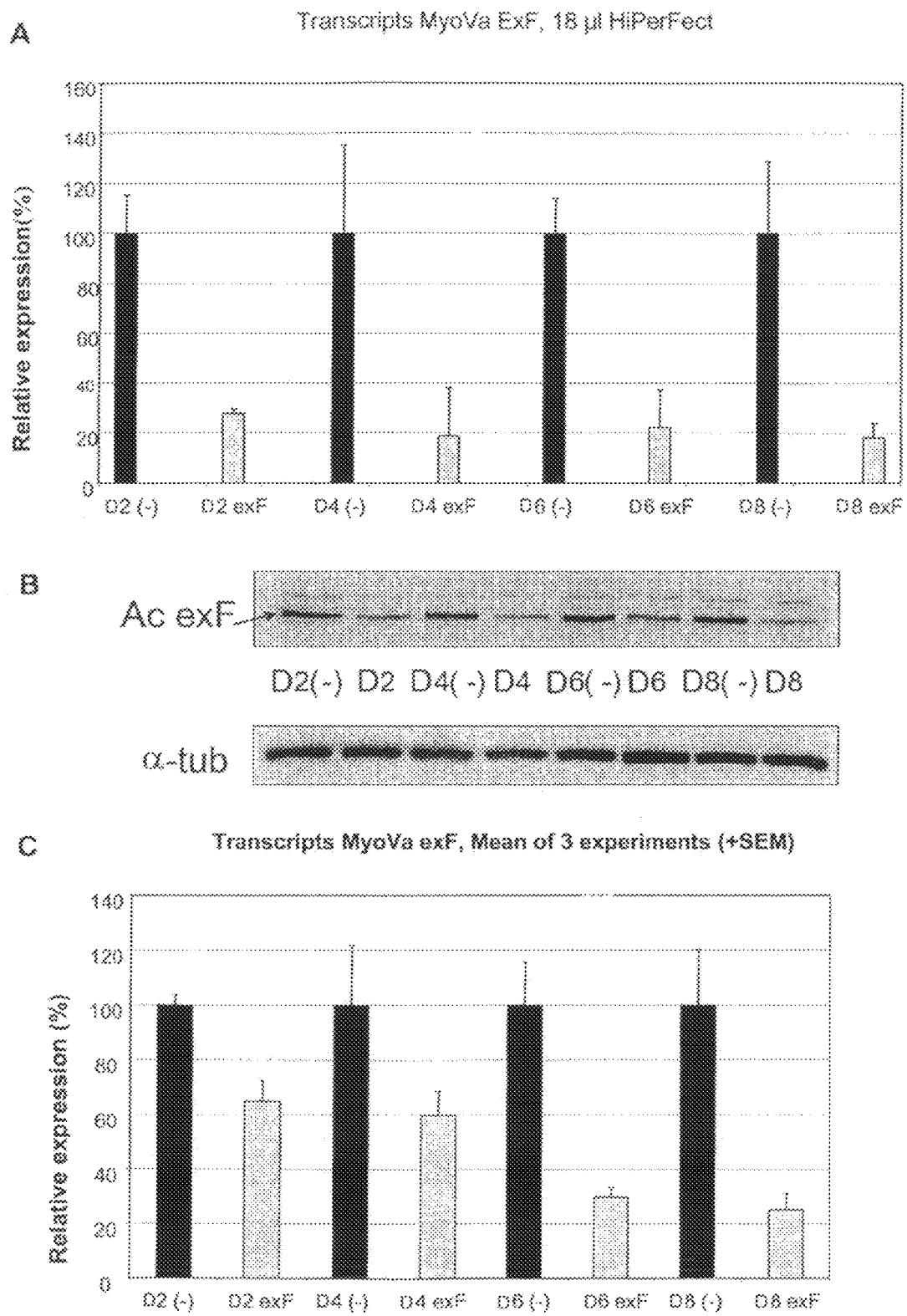
FIG. 9. Evaluation of the inhibition at RNA level and protein level during a long term experiment (D2, D4, D6, D8 after transfection). A. Analysis by quantitative real time PCR at RNA level B. Analysis at protein level by Western blot with an antibody directed specifically against the isoforms of the myosin Va protein comprising exon FC. Quantification carried out using Quantity One software, normalised compared with tubulin, all based on raw data.

The results are given in FIG. 9A and show that, compared to negative controls, a reduction of 72%, 81%, 78% and 82% was observed for the MyoVa exF transcripts at different points in time (D2, D4, D6 and D8 respectively).

At Protein Level

The results of the analysis of the cell lysates by Western blot are given in FIGS. 9B and C respectively showing the raw results from the Western blot and the quantification obtained with the Quantity One software (Biorad), and normalised with tubulin.

The results show that, as compared to negative controls, a reduction of 35%, 40%, 70% and 75% was observed for the MyoVa exF transcripts at different points in time (D2, D4, D6 and D8 respectively).

3.2.2 Effect of the Inhibition Caused by siRNA MyoVa exF n°:2 (SEQ ID NO:3) on the Location/Distribution of Melanosomes in PHEM It was shown above that MyoVa exF transcripts are involved in the capture of melanosomes in the subcortical actin network. Therefore the inhibition of MyoVa exF transcripts could result in decreased capture of melanosomes at the distal ends of the melanocyte dendrites, and possibly in a perinuclear accumulation of melanosomes.

In order to test this hypothesis, transfections with 25 nM of siRNA MyoVa exF n°:2 (SEQ ID NO:3) and 25 nM of a negative control siRNA were carried out on 300 000 PHEM plated on round glass slides. The PHEM were fixed in 3% paraformaldehyde at different points in time after transfection (day 3, day 6 and day 8).

Then, for immunohistochemistry experiments, the antibody specific to the exon F of myosin Va protein (dilution 1/500) (see above) was used in combination with a monoclonal antibody NKI-beteb (dilution 1/40) directed against the (pre)-melanosomal protein silver (Sanbio B. V., Uden, The Netherlands). Then the analysis was carried out by confocal microscopy.

Results:

Day 3 after Transfection

No difference was observed in the distribution of the melanosomes (present at the periphery and at the distal ends of the dendrites) for PHEM transfected with the negative control siRNA and PHEM transfected with siRNA MyoVa exF n°:2 (SEQ ID NO:3).

Day 6 after Transfection

Co-labelling with anti NKI-beteb antibodies and the anti myosin Va exon F antibody showed a change in the distribution of melanosomes in the PHEM transfected with siRNA MyoVa exF n°:2 (SEQ ID NO:3): melanosomes are mainly situated in the perinuclear area. Furthermore, the labelling of isoforms of the myosin Va protein comprising exon F was absent or weak at the distal ends of the dendrites.

Day 8 after Transfection

The same results were observed as at day 6.

Conclusion

Immunohistochemical analysis of PHEM transfected with siRNA MyoVa exF n°:2 (SEQ ID NO:3) or by a control siRNA with the anti NKI-beteb antibody and the anti myosin Va exon F antibody makes it possible to visualise the intracellular transport of melanosomes (by NKI-beteb) and also to detect the expression of the isoforms of the myosin Va protein comprising exon F.

The results obtained make it possible to conclude that the inhibition of the isoforms of the myosin Va protein comprising exon F leads to an abnormal distribution of melanosomes in the PHEM, that is to say a perinuclear distribution rather than a peripheral location with presence at the distal ends of the dendrites in the negative control, at days 6 to 8 after transfection.

3.3 Confirmation of the Inhibitory Effect of MyoVa exF Transcripts after PHEM Transfection with siRNA MyoVa n°:1 (SEQ ID NO:2)

In these experiments, a different siRNA, namely siRNA MyoVa n°:1 (SEQ ID NO:2) was used for the transfection of the PHEM so as to confirm that the inhibition is really specific to the exon F of the myosin Va protein and to exclude a non-specific artefact effect.

3.3.1 Evaluation of the Inhibition at RNA Level and Protein Level During a Long Term Experiment The same experiment as in paragraph 3.2.1 was repeated with siRNA MyoVa n°:1 (SEQ ID NO:2) in the place of siRNA MyoVa n°:2 (SEQ ID NO:3).

Figure 10:
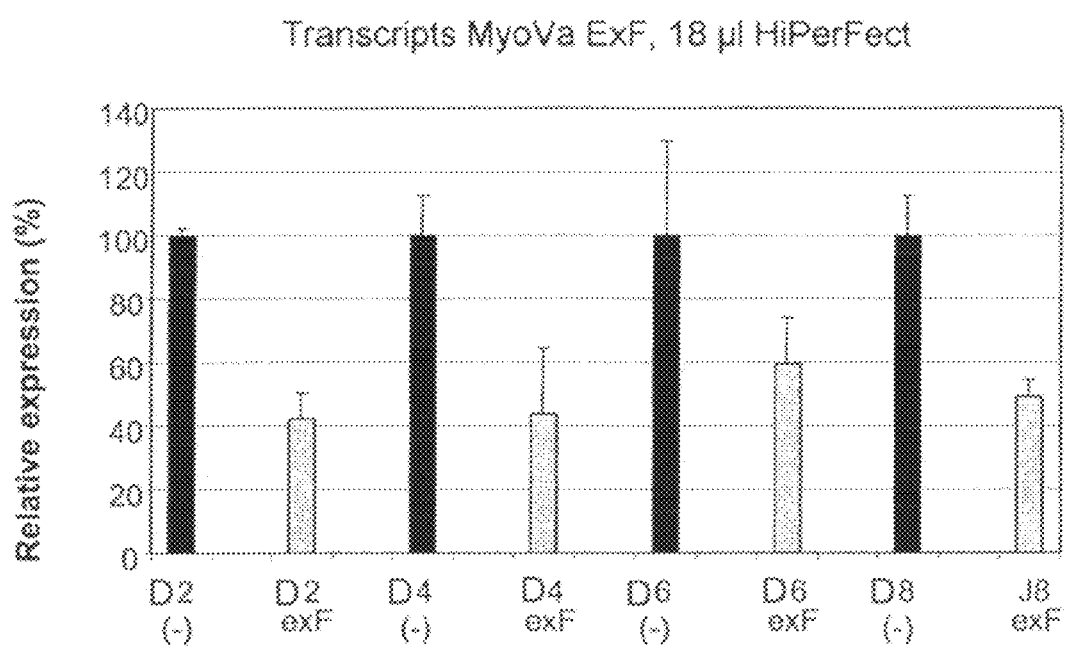
FIG. 10. Evaluation of the inhibition of transcripts comprising exon F (MyoVa exF transcripts) in PHEM transfected with siRNA MyoVa n°:1 (SEQ ID NO:2, exF) or the BLOCK-iT™ Fluorescent oligo oligonucleotide (siNEG) and 18 µl of HiPerFect reagent.

Results at RNA level are given in FIG. 10 and show a reduction of 58%, 59%, 41% and 51% at the different points in time (D2, D4, D6 and D8 respectively).

Furthermore, results obtained at the protein level correlated with those obtained for RNA (data not shown).

3.3.2 Effect of the Inhibition Caused by siRNA MyoVa exF n°:1 (SEQ ID NO:2) on the Location/Distribution of Melanosomes in the PHEM The same experiment as in paragraph 3.2.2 was repeated with siRNA MyoVa n°:1 (SEQ ID NO:2) in the place of siRNA MyoVa n°:2 (SEQ ID NO:3).

The results obtained on day 8 after transfection with the siRNA MyoVa n°:1 (SEQ ID NO:2) show, as for siRNA MyoVa n°:2 (SEQ ID NO:3), a perinuclear distribution of the melanosomes in the PHEM as compared to negative controls (data not shown).

3.3.3 Conclusions

Although the inhibition of the isoforms of the myosin Va protein comprising exon F (MyoVa exF transcripts) is less effective with siRNA MyoVa exF n°:1 (SEQ ID NO:2) than with siRNA MyoVa exF n°:2 (SEQ ID NO:3), the expression of MyoVa exF transcripts remains significantly reduced using siRNA MyoVa exF n°:1 (SEQ ID NO:2), at both the RNA and protein levels.

Furthermore, immunohistochemical analysis on fixed transfected PHEM also reveals disruption of the location and transport of melanosomes in the PHEM. It can therefore be concluded that the inhibition of the isoforms of the myosin Va protein comprising exon F and the observed phenotype effect caused by the use of siRNA MyoVa exF n°:1 and 2 (SEQ ID NO: 2 and 3) are specific and not artefacts.

Example 4

Inducing a Phenotype Effect by Long Term Inhibition of the Transcripts of the Myosin Va Protein Comprising Exon F (MyoVa exF Transcripts)

In order to obtain long term stable inhibition in PHEM of isoforms of myosin Va protein comprising exon F, lentiviral vectors expressing short hairpin RNA (or shRNA) directed against the exon F of myosin Va protein have been synthesised.

4.1 Materials and Methods

ShRNA sequences were developed from the siRNA sequence of the most effective siRNA for inhibiting the MyoVa exF, which is siRNA MyoVa n°:2 (comprising the RNA sequence with the gene sequence SEQ ID NO:3). More specifically, a double stranded oligonucleotide consisting of the following sequences was synthesised:

sense strand:
(SEQ ID NO: 15)
5'-GATCGTATCAATCATATCGGATTCTCAAGAGAAATCCGATATGATTG
ATACTTTTT-3' antisense strand:
(SEQ ID NO: 16)
5'-AGCTAAAAAGTATCAATCATATCGGATTTCTCTTGAGAATCCGATAT
GATTGATAC-3', wherein
the portions in bold correspond to the two complementary portions of the shRNA paired by Watson-Crick bonds, corresponding to the RNA with the genic sequence SEQ ID NO:3 of the sense strand of the siRNA MyoVa n°:2 and its complementary sequence,
the portion of sequence in normal type corresponds to the sequence with the hairpin structure linking the two complementary strands.
the underlined portion corresponds to a 5' overhang fragment making it possible to clone the double stranded oligonucleotide in an expression vector, and
the portion in italics corresponds to a transcription termination sequence initiated by an RNApolIII type H1 promoter.

This double stranded oligonucleotide was then cloned in a lentiviral vector under the control of an RNApolIII type H1 promoter.

This made it possible to produce in transfected cells shRNAs with the sequence:
5'-GUAUCAAUCAUAUCGGAUUCUCAA-GAGAAAUCCGAUAUGAUUGAU AC-3' (SEQ ID NO:17), where the portions in bold correspond to the two complementary portions paired by Watson-Crick bonds, corresponding to the RNA sequence with the gene sequence SEQ ID NO:3 of the sense strand of siRNA MyoVa n°:2 and its complementary sequence), and the portion in normal type corresponds to the sequence with the hairpin structure linking the two complementary strands.

Lentiviral vectors expressing scrambled shRNAs were also produced to be used as negative control. In this case, the sense and antisense strand sequences of the oligonucleotide cloned in the lentiviral vector controlled by an RNApolIII type H1 promoter were as follows:

sense strand:
(SEQ ID NO: 18)
5'-GATCATTATCTAGGAGATATCACCTCAAGAGAGTGATATCTCCTAGA
TAATTTTT-3' antisense strand:
(SEQ ID NO: 19)
5'-AGCTAAAAAATTATCTAGGAGATATCACTCTCTTGAGGTGATATCTC
CTAGATAAT-3' in which
the portions in bold correspond to the two complementary portions of the shRNA paired by Watson-Crick bonds, corresponding to the disordered bases of RNA sequence with the gene sequence SEQ ID NO:3 of the sense strand of the siRNA MyoVa n°:2 and its complementary sequence,
the portion of sequence in normal type corresponds to the sequence with the hairpin structure linking the two complementary strands.

the underlined portion corresponds to a 5' overhang fragment making it possible to clone the double stranded oligonucleotide in an expression vector, and the portion in italics corresponds to a transcription termination sequence initiated by an RNApolIII type H1 promoter.

This made it possible to produce in transfected cells shRNAs with the sequence:

5'-AUUAUCUAGGAGAUAUCACCUCAA-GAGAGUGAUAUCUCCUAGAUA A-3' (SEQ ID NO:20), where the portions in bold correspond to the two complementary portions of the shRNA paired by Watson-Crick bonds, (corresponding to the disordered bases of RNA sequence with the gene sequence SEQ ID NO:3 of the sense strand of the siRNA MyoVa n°:2 and its complementary sequence), and the portion in normal type corresponds to the sequence with the hairpin structure linking the two complementary strands.

4.2 Efficacy of Transduction

The efficacy of transduction in PHEM was determined by FACS analysis based on the presence of a GFP marker in the lentiviral vectors mentioned above.

The transduction of 100 000 PHEM with lentiviruses at a multiplicity of infection (MOI) of 10 leads to an efficacy of transduction of 90% after two cycles of infection.

4.3 Evaluation of the Inhibition at RNA Level and Protein Level

In order to evaluate the effect of inhibition at the RNA level and at the protein level, 600 000 PHEM were transduced at an MOI of 10 with lentiviral vectors comprising shRNAs MyoVa exF n°:2 or scrambled shRNAs (negative control) respectively.

The results show, at both RNA level and at protein level, a large reduction of isoforms of the myosin Va protein comprising exon F in the transduced cells with the lentiviral vectors comprising shRNAs MyoVa exF n°:2 as compared to negative control.

4.4 Effect of the Inhibition on the Transport of Melanosomes

Subsequently, an immunohistochemical analysis of PHEM transduced with lentiviral vectors comprising shRNAs MyoVa exF n°:2 or scrambled shRNAs (negative control) was carried out. The results show a perinuclear distribution of the melanosomes in the PHEM transduced with lentiviral vectors comprising shRNAs MyoVa exF n°:2 as compared to e negative control.

These results confirm the effects observed previously in the case of inhibition of the MyoVa exF transcripts by the use of synthetic siRNAs.

4.5 Effect of the Inhibition of MyoVa exF Transcripts on the Transfer of Melanin from the Melanocytes to the Keratinocytes in a 3D Model of Reconstructed Epidermis.

50 000 PHEM were transduced with the lentiviral vectors expressing the shRNAs MyoVa exF n°:2. These stably transduced PHEM were introduced, with 500 000 keratinocytes, into a reconstructed skin model. PHEM stably transduced with lentiviral vectors expressing scrambled shRNAs were used as negative control. The reconstructed skin was then irradiated or not with UV simulating the sun.

Visual inspection of the reconstructed skin showed that no increase in pigmentation was observed after irradiation for the skin comprising PHEM transduced with lentiviral vectors expressing the shRNAs MyoVa exF n°:2, contrary to the skin comprising PHEM transduced with lentiviral vectors expressing scrambled shRNAs. A quantitative evaluation of the pigmentation by Fontana-Masson staining and digital colour image analysis then made it possible to confirm these observations.

The distribution of melanosomes in the melanocytes and the keratinocytes was then examined by electron microscopy. These analyses showed a stimulation of the transfer of pigments from melanocytes to keratinocytes in the reconstructed skin irradiated with UV and comprising PHEM transduced with lentiviral vectors expressing the scrambled shRNAs, compared with the same non-irradiated skin. On the contrary, in reconstructed skin irradiated with UV and comprising PHEM transduced with lentiviral vectors expressing shRNAs MyoVa exF n°:2, only a reduced transfer of melanin was observed as compared to non-irradiated control skin.

4.6 Conclusions

Thus, results show that a stable transfection of PHEM with lentiviral vectors expressing a shRNA specifically targeting the exon F of human myosin Va protein enables significant interference with the quantity of MyoVa exF transcripts and isoforms of myosin Va protein comprising exon F, and with the transport of melanosomes and their transfer from melanocytes to keratinocytes.

The invention claimed is:

1. An isolated siRNA comprising a sense RNA strand and a complementary antisense RNA strand which together form an RNA duplex, wherein the sense RNA strand comprises a sequence selected from the group consisting of SEQ ID NO:2, SEQ ID NO:3, and SEQ ID NO:4.

2. The siRNA according to claim 1, wherein said sense strand comprises or consists of the nucleotide sequence SEQ ID NO:3.

3. An isolated siRNA comprising a sense RNA strand and a complementary antisense RNA strand which together form an RNA duplex, wherein said siRNA is a shRNA consisting of a single molecule of single stranded RNA in which two complementary portions are paired by Watson-Crick bonds and are linked covalently on one side by a hairpin type structure, wherein said shRNA comprises or consists of the sequence SEQ ID NO:17.

4. The siRNA according to claim 1, wherein the sense and/or antisense RNA strands further comprises a 3' overhang fragment of 2 to 4 natural or modified LNA type nucleotides.

5. The siRNA according to claim 1, wherein the sense RNA strand and/or the antisense RNA strand comprise at least one chemical modification in their sugar portions, their nucleobase portions or their internucleotide backbone.

6. A cosmetic agent comprising the siRNA according to claim 1.

7. A drug comprising the siRNA according to claim 1.

8. A composition comprising at least one siRNA according to claim 1 and an acceptable carrier.

9. The composition according to claim 8, which is administered topically.

10. The composition according to claim 8, wherein it further comprises at least one depigmenting agent.

11. The siRNA according to claim 1, wherein said sense strand comprises or consists of the nucleotide sequence SEQ ID NO:4.

12. The siRNA according to claim 1, wherein said sense strand comprises or consists of the nucleotide sequence SEQ ID NO:2.

13. The siRNA according to claim 1, wherein both complementary strands of said siRNA comprise the same 3' overhang fragment of 2 nucleotides with the sequence "TT".

14. A composition comprising at least one siRNA according to claim 13 and an acceptable carrier.

* * * * *

SEQUENCE LISTING

```
<160> NUMBER OF SEQ ID NOS: 21

<210> SEQ ID NO 1
<211> LENGTH: 75
<212> TYPE: DNA
<213> ORGANISM: homo sapiens
<220> FEATURE:
<221> NAME/KEY: misc_feature
<223> OTHER INFORMATION: Sequence of human myosin Va protein exon F

<400> SEQUENCE: 1
tattttgagg aattatatgc agatgaccct aagaagtatc aatcatatcg gatttccctt      60
tacaaacgga tgatt                                                      75

<210> SEQ ID NO 2
<211> LENGTH: 19
<212> TYPE: DNA
<213> ORGANISM: homo sapiens
<220> FEATURE:
```

```
<221> NAME/KEY: misc_feature
<223> OTHER INFORMATION: Fragment of human myosin Va protein exon F

<400> SEQUENCE: 2
tgaccctaag aagtatcaa                                                19

<210> SEQ ID NO 3
<211> LENGTH: 19
<212> TYPE: DNA
<213> ORGANISM: homo sapiens
<220> FEATURE:
<221> NAME/KEY: misc_feature
<223> OTHER INFORMATION: Fragment of human myosin Va protein exon F

<400> SEQUENCE: 3
gtatcaatca tatcggatt                                                19

<210> SEQ ID NO 4
<211> LENGTH: 19
<212> TYPE: DNA
<213> ORGANISM: homo sapiens
<220> FEATURE:
<221> NAME/KEY: misc_feature
<223> OTHER INFORMATION: Fragment of human myosin Va protein exon F

<400> SEQUENCE: 4
tcatatcgga tttcccttt                                                19

<210> SEQ ID NO 5
<211> LENGTH: 19
<212> TYPE: DNA
<213> ORGANISM: Artificial sequence
<220> FEATURE:
<223> OTHER INFORMATION: Synthetic sense amplification primer of human
     myosin Va protein exon F

<400> SEQUENCE: 5
cagcctgcag cacgagatc                                                19

<210> SEQ ID NO 6
<211> LENGTH: 27
<212> TYPE: DNA
<213> ORGANISM: Artificial sequence
<220> FEATURE:
<223> OTHER INFORMATION: Synthetic antisense amplification primer of
     human myosin Va protein exon F

<400> SEQUENCE: 6
tcttagggtc atctgcatat aattcct                                       27

<210> SEQ ID NO 7
<211> LENGTH: 23
<212> TYPE: DNA
<213> ORGANISM: Artificial sequence
<220> FEATURE:
<223> OTHER INFORMATION: Synthetic sense amplification primer of the GP
     part of human myosin Va protein

<400> SEQUENCE: 7
gcagtcaatt tgattccagg att                                           23

<210> SEQ ID NO 8
<211> LENGTH: 25
<212> TYPE: DNA
<213> ORGANISM: Artificial sequence
<220> FEATURE:
<223> OTHER INFORMATION: Synthetic antisense amplification primer of the
     GP part of human myosin Va protein
```

-continued

<210> SEQ ID NO 8
<211> LENGTH: 21
<212> TYPE: DNA
<213> ORGANISM: Artificial sequence
<220> FEATURE:
<223> OTHER INFORMATION: Synthetic sense strand of anti-myosin Va siRNA
      no. 1

<400> SEQUENCE: 8
tgatcatcat tcaggtagtc agcat                                         25

<210> SEQ ID NO 9
<211> LENGTH: 21
<212> TYPE: DNA
<213> ORGANISM: Artificial sequence
<220> FEATURE:
<223> OTHER INFORMATION: Synthetic sense strand of anti-myosin Va siRNA
      no. 1

<400> SEQUENCE: 9
ugacccuaag aaguaucaat t                                             21

<210> SEQ ID NO 10
<211> LENGTH: 21
<212> TYPE: DNA
<213> ORGANISM: Artificial sequence
<220> FEATURE:
<223> OTHER INFORMATION: Synthetic antisense strand of anti-myosin Va
      siRNA no. 1

<400> SEQUENCE: 10
uugauacuuc uuagggucat t                                             21

<210> SEQ ID NO 11
<211> LENGTH: 21
<212> TYPE: DNA
<213> ORGANISM: Artificial sequence
<220> FEATURE:
<223> OTHER INFORMATION: Synthetic sense strand of anti-myosin Va siRNA
      no. 2

<400> SEQUENCE: 11
guaucaauca uaucggauut t                                             21

<210> SEQ ID NO 12
<211> LENGTH: 21
<212> TYPE: DNA
<213> ORGANISM: Artificial sequence
<220> FEATURE:
<223> OTHER INFORMATION: Synthetic antisense strand of anti-myosin Va
      siRNA no. 2

<400> SEQUENCE: 12
aauccgauau gauugauact t                                             21

<210> SEQ ID NO 13
<211> LENGTH: 21
<212> TYPE: DNA
<213> ORGANISM: Artificial sequence
<220> FEATURE:
<223> OTHER INFORMATION: Synthetic sense strand of anti-myosin Va siRNA
      no. 3

<400> SEQUENCE: 13
ucauaucgga uuucccuuut t                                             21

<210> SEQ ID NO 14
<211> LENGTH: 21
<212> TYPE: DNA
<213> ORGANISM: Artificial sequence
<220> FEATURE:
<223> OTHER INFORMATION: Synthetic antisense strand of anti-myosin Va
      siRNA no. 3

<400> SEQUENCE: 14

```
aaagggaaau ccgauaugat t                                              21

<210> SEQ ID NO 15
<211> LENGTH: 56
<212> TYPE: DNA
<213> ORGANISM: Artificial sequence
<220> FEATURE:
<223> OTHER INFORMATION: Synthetic sense strand oligonucleotide for the
      cloning of an anti-myosin Va shRNA in a lentiviral carrier

<400> SEQUENCE: 15
gatcgtatca atcatatcgg attctcaaga gaaatccgat atgattgata cttttt         56

<210> SEQ ID NO 16
<211> LENGTH: 56
<212> TYPE: DNA
<213> ORGANISM: Artificial sequence
<220> FEATURE:
<223> OTHER INFORMATION: Synthetic antisense strand oligonucleotide for
      the cloning of an anti-myosin Va shRNA in a lentiviral carrier

<400> SEQUENCE: 16
agctaaaaag tatcaatcat atcggatttc tcttgagaat ccgatatgat tgatac         56

<210> SEQ ID NO 17
<211> LENGTH: 47
<212> TYPE: RNA
<213> ORGANISM: Artificial sequence
<220> FEATURE:
<223> OTHER INFORMATION: Synthetic anti-myosin Va shRNA

<400> SEQUENCE: 17
guaucaauca uaucggauuc ucaagagaaa uccgauauga uugauac                   47

<210> SEQ ID NO 18
<211> LENGTH: 55
<212> TYPE: DNA
<213> ORGANISM: Artificial sequence
<220> FEATURE:
<223> OTHER INFORMATION: Synthetic sense strand oligonucleotide for the
      cloning of an interfered control shRNA in a lentiviral vector

<400> SEQUENCE: 18
gatcattatc taggagatat cacctcaaga gagtgatatc tctagataa ttttt           55

<210> SEQ ID NO 19
<211> LENGTH: 56
<212> TYPE: DNA
<213> ORGANISM: Artificial sequence
<220> FEATURE:
<223> OTHER INFORMATION: Synthetic antisense strand oligonucleotide for
      the cloning of an interfered control shRNA in a lentiviral vector

<400> SEQUENCE: 19
agctaaaaaa ttatctagga gatatcactc tcttgaggtg atatctccta gataat         56

<210> SEQ ID NO 20
<211> LENGTH: 46
<212> TYPE: RNA
<213> ORGANISM: Artificial sequence
<220> FEATURE:
<223> OTHER INFORMATION: Synthetic interfered control shRNA

<400> SEQUENCE: 20
auuaucuagg agauaucacc ucaagagagu gauaucccu agauaa                     46
```

-continued

```
<210> SEQ ID NO 21
<211> LENGTH: 693
<212> TYPE: DNA
<213> ORGANISM: Homo sapiens

<400> SEQUENCE: 21
cgtcaagaac tagaatcaga aaacaaaaaa ctgaagaatg agctaaatga gttgcgcaag      60
gccctcagtg agaaaagtgc cccagaggtg accgccccag gtgcacctgc ctaccgtgtc     120
ctcatggagc agctgacctc tgtgagcgag gagcttgatg tccgcaagga ggaagtcctc     180
atcttaaggt ctcaactggt gagccagaaa gaggccatcc aacccaagga tgacaagaat     240
acaatgacag attccacaat acttttggaa gatgtacaaa aaatgaaaga taaaggtgaa     300
atagcacaag catacattgg tttgaaagaa acaaatagat catctgctct ggattaccat     360
gagttgaatg aggatggaga gctgtggctg gtttatgaag ggttaaaaca agccaacagg     420
ctcctggaat cccagctgca gtcacagaag aggagccatg agaatgaggc cgaggccctc     480
cgtggggaga tccagagcct gaaggaggag aacaaccgac agcagcagct gctggcccag     540
aacctgcagc tgcccccaga ggcccgcatt gaggccagcc tgcagcacga gatcacccgg     600
ctgaccaacg aaaacttgta ttttgaggaa ttatatgcag atgaccctaa gaagtatcaa     660
tcatatcgga tttcccttta caaacggatg att                                  693
```